United States Patent [19]

Meyer et al.

[11] Patent Number: 4,629,810
[45] Date of Patent: Dec. 16, 1986

[54] PHENYL SULFONAMIDES

[75] Inventors: Willy Meyer, Riehen; Werner Föry, Basel, both of Switzerland

[73] Assignee: Ciba-Geigy Corporation, Ardsley, N.Y.

[21] Appl. No.: 693,481

[22] Filed: Jan. 22, 1985

Related U.S. Application Data

[62] Division of Ser. No. 417,743, Sep. 13, 1982, Pat. No. 4,510,325, which is a division of Ser. No. 282,847, Jul. 13, 1981, abandoned.

[30] Foreign Application Priority Data

Jul. 17, 1980 [CH] Switzerland .......... 5481/80
Nov. 5, 1980 [CH] Switzerland .......... 8216/80
Jun. 17, 1981 [CH] Switzerland .......... 3991/81

[51] Int. Cl.⁴ .......... C07C 143/78
[52] U.S. Cl. .......... 564/89
[58] Field of Search .......... 564/89

[56] References Cited

FOREIGN PATENT DOCUMENTS 2246403 3/1973 Fed. Rep. of Germany ........ 564/89

OTHER PUBLICATIONS

Huntress et al., J.A.C., 62, pp. 603–604, Mar. 1940.
Bartram et al., J. Chem. Soc., pp. 2903–2904, (1958).
Houben-Weyl, "Methoden der Organischem Chemie," vol. IX, p. 607, 1955.
Tetrahedron Letter, 1972, pp. 251–254.
Chem. Ber. 105, 2791–2799, (1972).

Primary Examiner—Charles F. Warren
Assistant Examiner—Carolyn Greason
Attorney, Agent, or Firm—Edward McC. Roberts; Bruce M. Collins

[57] ABSTRACT

N-phenylsulfonyl-N'-pyrimidinyl- and -triazinylureas of the general formula

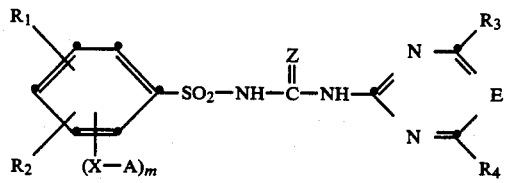

and the salts thereof with amines, alkali metal or alkaline earth metal bases or with quaternary ammonium bases, have good pre- and postemergence selective herbicidal and growth regulating properties. In the above formula A is a $C_1-C_6$alkyl radical which is substituted by $C_1-C_4$alkoxy, $C_1-C_4$alkylthio, $C_1-C_4$alkylsulfinyl, $C_1-C_4$alkylsulfonyl, $C_1-C_4$haloalkoxy, $C_1-C_4$haloalkylthio, $C_1-C_4$haloalkylsulfinyl or $C_1-C_4$haloalkylsulfonyl, or a $C_2-C_6$alkenyl radical which is unsubstituted or substituted by the above substituents, or is a $C_2-C_6$haloalkenyl radical, E is the methine group or nitrogen, X is oxygen, sulfur, a sulfinyl or sulfonyl bridge, Z is oxygen or sulfur, m is 1 or 2, $R_1$ is hydrogen, halogen, $C_1-C_5$alkyl, $C_2-C_5$alkenyl or a radical $-Y-R_5$, $R_2$ is hydrogen, halogen, $C_1-C_5$alkyl, $C_2-C_5$alkenyl, $C_1-C_4$haloalkyl, or a radical $-Y-R_5$, $-COOR_6$, $-NO_2$ or $-CO-NR_7-R_8$, $R_3$ and $R_4$, each independently of the other, are hydrogen, $C_1-C_4$alkyl, $C_1-C_4$alkoxy, $C_1-C_4$alkylthio, $C_1-C_4$haloalkyl, halogen or alkoxyalkyl of at most 4 carbon atoms, $R_5$ and $R_6$, each independently of the other, are $C_1-C_5$alkyl, $C_2-C_5$alkenyl or $C_2-C_6$alkynyl, $R_7$ and $R_8$, each independently of the other, are hydrogen, $C_1-C_5$alkyl, $C_2-C_5$alkenyl or $C_2-C_6$alkynyl, and Y is oxygen, sulfur, a sulfinyl or sulfonyl bridge.

2 Claims, No Drawings

PHENYL SULFONAMIDES

This is a division of application Ser. No. 417,743, filed on Sept. 13, 1982, now U.S. Pat. No. 4,510,325, issued Apr. 9, 1985, which is a division of application Ser. No. 282,847 filed on July 13, 1981, now abandoned.

The present invention relates to novel N-phenylsulfonyl-N'-pyrimidinyl- and triazinylureas having herbicidal and plant growth-regulating properties, to the production thereof, to compositions containing them, and to the use thereof for controlling weeds, in particular selectively, in crops of useful plants, or for regulating and inhibiting plant growth. The invention also relates to novel phenylsulfonamides prepared as intermediates.

The N-phenylsulfonyl-N'-pyrimidinyl- and -triazinylureas of this invention have the general formula I

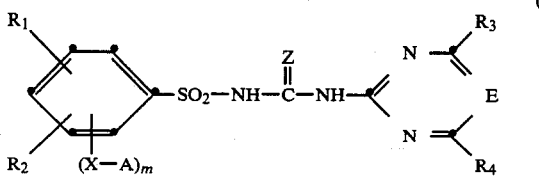

wherein
A is a $C_1$–$C_6$alkyl radical which is substituted by $C_1$–$C_4$alkoxy, $C_1$–$C_4$alkylthio, $C_1$–$C_4$alkylsulfinyl, $C_1$–$C_4$alkylsulfonyl, $C_1$–$C_4$haloalkoxy, $C_1$–$C_4$haloalkylthio, $C_1$–$C_4$haloalkylsulfinyl, or $C_1$–$C_4$haloalkylsulfonyl, or a $C_2$–$C_6$alkenyl radical which is unsubstituted or substituted by the above substituents, or is a $C_2$–$C_6$haloalkenyl radical,
E is the methine group or nitrogen,
X is oxygen, sulfur, a sulfinyl or sulfonyl bridge,
Z is oxygen or sulfur,
m is 1 or 2,
$R_1$ is hydrogen, halogen, $C_1$–$C_5$alkyl, $C_2$–$C_5$alkenyl or a radical —Y—$R_5$,
$R_2$ is hydrogen, halogen, $C_1$–$C_5$alkyl, $C_2$–$C_5$alkenyl, $C_1$–$C_4$haloalkyl, or a radical —Y—$R_5$, —COO$R_6$, —NO$_2$ or —CO—N$R_7$—$R_8$,
$R_3$ and $R_4$, each independently of the other, are hydrogen, $C_1$–$C_4$alkyl, $C_1$–$C_4$alkoxy, $C_1$–$C_4$alkylthio, $C_1$–$C_4$haloalkyl, halogen or alkoxyalkyl of at most 4 carbon atoms,
$R_5$ and $R_6$, each independently of the other, are $C_1$–$C_5$alkyl, $C_2$–$C_5$alkenyl or $C_2$–$C_6$alkynyl,
$R_7$ and $R_8$, each independently of the other, are hydrogen, $C_1$–$C_5$alkyl, $C_2$–$C_5$alkenyl or $C_2$–$C_6$alkynyl, and
Y is oxygen, sulfur, a sulfinyl or sulfonyl bridge, and salts of these compounds.

Herbicidally active ureas, triazines and pyrimidines are generally known in the art. Arylsulfamoyl-heterocyclylaminocarbamoyl compounds with herbicidal and plant growth-regulating action have recently been described, for example in European patent publication Nos. 1514 and 1515, U.S. Pat. No. 4,127,405, German Offenlegungsschrift No. 2 715 786 or French patent specification No. 1 468 747.

In the above definitions, alkyl denotes straight-chain or branched alkyl, e.g. methyl, ethyl, n-propyl, isopropyl, the four isomers of butyl, n-amyl, isoamyl, 2-amyl, 3-amyl, n-hexyl or isohexyl, with straight-chain alkyl being preferred.

Alkoxy denotes methoxy, ethoxy, n-propyloxy, isopropyloxy and the four butyloxy isomers, and is, in particular, methoxy or ethoxy.

Alkylthio is e.g. methylthio, ethylthio, n-propylthio, isopropylthio and n-butylthio, with methylthio and ethylthio being preferred.

Examples of alkenyl radicals are vinyl, allyl, isopropenyl, 1-propenyl, 1-butenyl, 2-butenyl, 3-butenyl, 1-isobutenyl, 2-isobutenyl, 1-pentenyl, 2-pentenyl, 3-pentenyl and 4-pentenyl, with vinyl, allyl and 4-pentenyl being preferred.

Alkylsulfinyl is e.g. methylsufinyl, ethylsulfinyl, n-propylsulfinyl and n-butylsulfinyl, with methylsulfinyl and ethylsulfinyl being preferred.

Alkylsulfonyl is e.g. methylsulfonyl, ethylsulfonyl, n-propylsulfonyl and n-butylsulfonyl, with methylsulfonyl and ethylsulfonyl being preferred.

Halogen in the definitions of $R_1$ to $R_4$ and in haloalkoxy, haloalkylsulfinyl, haloalkylsulfonyl, haloalkylthio and haloalkenyl is fluorine, chlorine and bromine, with fluorine and chlorine being preferred.

The invention also comprises the salts which the compounds of formula I are able to form with amines, alkali metal and alkaline earth metal bases or quaternary ammonium bases.

Preferred salt-forming alkali metal and alkaline earth metal hydroxides are the hydroxides of lithium, sodium, potassium, magnesium or calcium, most preferably of sodium or potassium.

Examples of suitable salt-forming amines are primary, secondary and tertiary aliphatic and aromatic amines such as methylamine, ethylamine, propylamine, isopropylamine, the four isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine and diethanolamine being most preferred.

Examples of quaternary ammonium bases are, in general, the cations of haloammonium salts, e.g. the tetramethylammonium cation, the trimethylbenzylammonium cation, the triethylbenzylammonium cation, the tetraethylammonium cation, the trimethylethylammonium cation, and also the ammonium cation.

Preferred compounds of the formula I are those in which
(a) Z is oxygen and
(b) $R_3$ and $R_4$ together contain not more than 4 carbon atoms.

Group (a) can be divided into two further subgroups which consist of compounds in which
(aa) m is 1, and
(ab) m is 2.

Preferred compounds in group (aa) are those in which the radical —X—A is in the 2- or 3-position to the sulfonyl radical. Among these preferred compounds further preference attaches to those compounds in which the radical —X—A is in the 2-position.

A preferred group of compounds in group (ab) comprises those compounds in which both radicals —X—A are in the 2 and 5-position to the sulfonyl group.

A further preference in connection with compounds of the above subgroups (aa) and (ab) consists in the feature that the radicals $R_3$ and $R_4$ together contain at most 4 carbon atoms. Accordingly, particularly preferred groups of compounds of formula I are the groups
(aab) in which only one radical —X—A is in the 2-position to the sulfonyl radical, Z is oxygen and R3 and R4 together contain not more than 4 carbon atoms, and
(abb) in which two radicals —X—A are in the 2- and 5-position to the sulfonyl radical, Z is oxygen and R3 and R4 together contain not more than 4 carbon atoms.

Preferred compounds of the group (aab) are those in which $R_1$ is hydrogen and $R_2$ is in the 5- or 6-position to the sulfonyl group. Among these preferred compounds, preference attaches in turn to those compound in which $R_2$ is hydrogen, halogen, $C_1-C_4$alkoxy, nitro or $COOR_6$.

Further preferred compounds within this last mentioned group are those in which $R_2$ is hydrogen, fluorine, nitro or $C_1-C_4$alkoxy, and each of $R_3$ and $R_4$ is hydrogen, $C_1-C_4$alkyl, $C_1-C_4$alkoxy, $C_1-C_4$alkylthio, halogen or alkoxyalkyl, whilst $R_3$ and $R_4$ together contain at most 4 carbon atoms.

Among these compounds, preferred compounds are in turn those in which $R_2$ is hydrogen and each of $R_3$ and $R_4$ is $C_1-C_4$alkyl, $C_1-C_4$alkoxy, methylthio, halogen or alkoxyalkyl.

Further preferred compounds within this last mentioned group are those in which X is oxygen or sulfur. Of these compounds, the most preferred are in turn those in which A is $C_2-C_8$alkoxyalkyl, $C_2-C_4$haloalkenyl or $C_2-C_6$alkenyl.

Three preferred subgroups of compounds belonging to this last group are those in which
(α) A is $C_2-C_8$alkoxyalkyl and each of $R_3$ and $R_4$ is methyl, ethyl, chlorine or methoxy,
(β) A is $C_2-C_6$alkenyl and each of $R_3$ and $R_4$ is methyl, ethyl, chlorine or methoxy, and
(γ) A is vinyl substituted by 1 to 3 halogen atoms and each of $R_3$ and $R_4$ is methyl, ethyl, chlorine or methoxy.

Of the compounds of formula I in which Z is sulfur, those compounds are preferred in which X is oxygen or sulfur, $R_3$ and $R_4$, each independently of the other, are $C_1-C_3$alkyl, $C_1-C_3$alkoxy or $C_1-C_3$alkylthio, containing together at most 4 carbon atoms, and A is —CH$_2$—CH=CH$_2$, —CH$_2$—CH=CH—CH$_3$, —CH$_2$—CH(CH$_3$)=CH$_2$, methoxyethyl, methoxymethyl or —CCl=CHCl, and the radical —X—A is in the 2-position and m is 1.

A preferred individual compound is N-(2-allyloxyphenylsulfonyl)-N'-(4-methoxy-6-methyl-1,3,5-triazin-2-yl)urea.

The process for obtaining the compounds of formula I is carried out in an inert organic solvent.

In a first process, the compounds of the formula I are obtained by reacting a phenylsulfonamide of the formula II

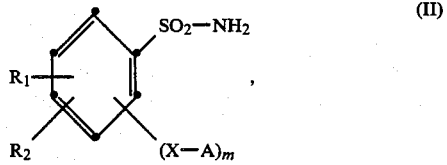

wherein A, $R_1$, $R_2$, X and m are as defined for formula I, in the presence of a base, with a N-pyrimidinyl- or N-triazinylcarbamate of the formula III

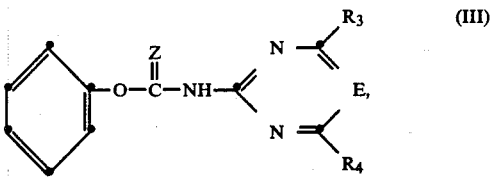

wherein E, $R_3$, $R_4$ and Z are as defined for formula I.

In a second process, compounds of formula I are obtained by reacting a phenylsulfonylisocyanate or phenylsulfonylisothiocyanate of the formula IV

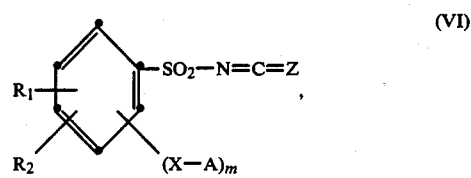

wherein A, $R_1$, $R_2$, m, X and Z are as defined for formula I, optionally in the presence of a base, with an amine of the formula V

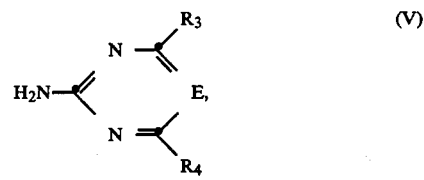

wherein E, $R_3$ and $R_4$ are as defined for formula I.

In a further process, the compounds of formula I are obtained by reacting a sulfonamide of the formula II above, optionally in the presence of a base, with an isocyanate or isothiocyanate of the formula VI

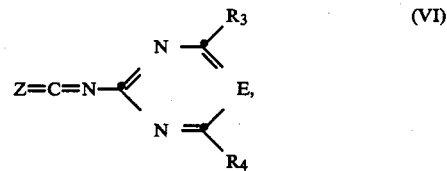

wherein E, $R_3$, $R_4$ and Z are as defined for formula I.

Finally, the compounds of formula I can also be obtained by reacting a N-phenylsulfonylcarbamate of the formula VII

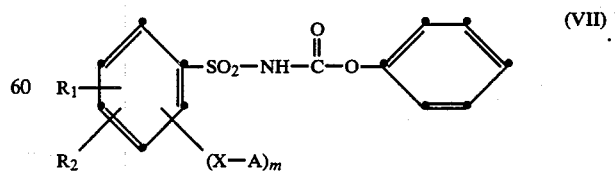

wherein A, $R_1$, $R_2$, m and X are as defined for formula I, with an amine of the formula V above.

If desired, the ureas of formula I can be converted into salts with amines, alkali metal or alkaline earth metal hydroxides or quaternary ammonium bases. This conversion is carried out e.g. by reacting the compounds of formula I with the equimolar amount of a base and removing the solvent by evaporation.

Some of the starting materials of the formulae II, IV and VII are novel and can be prepared by the following methods.

The novel sulfonamides of formula II used as intermediates are obtained from the corresponding anilines by diazotisation and replacement of the diazo group, with sulfur dioxide, in the presence of a catalyst such as copper(I) chloride, in hydrochloric acid or acetic acid, and reacting the resultant phenylsulfonyl chloride with ammonium hydroxide solution.

The compounds of formula II can also be obtained by O- or S-alkylation or O- or S-alkenylation of hydroxy- or thiophenylsulfonamides with the corresponding halides or sulfuric acid esters, or by reaction of ortho-halo-phenylsulfonamides with metal alcoholates or mercaptides and, if desired, by oxidation thereof e.g. with periodates or peracids to give the corresponding sulfoxides and sulfones.

Ortho-hydroxyphenylsulfonamides or substituted ortho-hydroxyphenylsulfonamides of the formula VIII

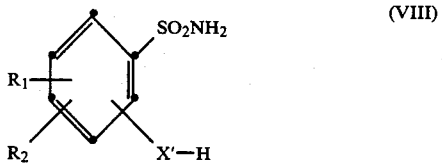
(VIII)

wherein $R_1$ and $R_2$ are as defined for formula I and $X'$ is oxygen or sulfur, as starting materials of specific sulfonamides of the formula II, are novel, with the exception of ortho-hydroxyphenylsulfonamide. They can be obtained by ether cleavage of corresponding $C_1$–$C_4$alkoxyphenylsulfonamides, e.g. with boron trihalides [such reactions are described in U.S. Pat. No. 3,904,680 and in J. Am. Chem. Soc, 64, 1128 (1942)] or by hydrogenolysis of the corresponding benzylphenylsulfonamides, as described in J. Chem. Soc. 1958, 2903.

The alkoxyphenylsulfonamides can, in turn, be obtained from the corresponding alkoxyanilides, as already mentioned, or by chlorosulfonylation of alkoxybenzenes and reaction of the resultant phenylsulfonyl chlorides with ammonium hydroxide solution. Such reactions are known from from J. Am. Chem. Soc. 62, 603 (1940).

The compounds of formulae II and VIII employed as intermediates are novel, or some are novel, and have been specially developed for the synthesis of compounds of formula I. These intermediates constitute a further object of the invention.

The phenylsulfonylisocyanates of the formula IV can be obtained by reacting the sulfonamides of the formula II with phosgene, in the presence of butylisocyanate in a chlorinated hydrocarbon as solvent, at reflux temperature. Similar reactions are described in "Newer Methods of Preparative Organic Chemistry", Vol. VI, 223–241, Academic Press, New York and London.

The isothiocyanates of the formula IV are obtained by treating the sulfonamides of formula II with carbon disulfide and potassium hydroxide and by subsequent reaction of the dipotassium salt with phosgene. Such processes are described in Arch. Pharm. 299, 174 (1966).

The N-phenylsulfonylcarbamates of the formula VII are obtained by reacting the sulfonamides of the formula II with diphenyl carbonate in the presence of a base. Similar processes are described in Japanese patent specification No. 61 169.

The starting materials of the formulae III, V and VI are known or they can be prepared by known methods.

Isocyanates of the formula VI can be prepared by reacting amines of the formula V with oxalyl chloride in a chlorinated hydrocarbon as solvent. Amines of the formula V are known and some are commercially available, or they can be prepared by known methods, q.v. "The Chemistry of Heterocyclic Compounds", Vol. XIV, Interscience Publishers, New York, London.

It is expedient to carry out the reactions for obtaining compounds of formula I in aprotic, inert organic solvents such as methylene chloride, tetrahydrofurane, acetonitrile, dioxane or toluene.

The reaction temperatures are preferably in the range from $-20°$ and $+120°$ C. The reactions are normally slightly exothermic and can be carried out at room temperature. To shorten the reaction time or also to initiate the reaction it is expedient to heat the reaction mixture briefly to boiling point. The reaction times can also be shortened by addition of a few drops of a base or isocyanate as catalyst.

The final products can be isolated by concentrating the reaction mixture and/or removing the solvent by evaporation, and by recrystallisation or by triturating the solid residue in solvents in which it is poorly soluble, such as ether, aromatic hydrocarbons or chlorinated hydrocarbons.

The compounds of formula I are stable compounds, and no protective measures are required for handling them.

The compounds of formula I have pronounced plant growth-regulating, especially plant growth-inhibiting, properties. The growth of both monocots and dicots is inhibited. Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Further, the compounds of formula I are suitable for preventing stored potatoes from seeding. During winter storage, potatoes often develop sprouts which result in shrinkage, weight loss, and rot.

When the compounds of formula I are applied in higher rates of application, all tested plants are so damaged in their development that they wither. When used in lower rates of application, the compounds of formula I have good selective growth-inhibiting and selective herbicidal properties which make them most suitable for use in crops of useful plants, especially in cereals, cotton, soybeans, maize and rice. In some cases damage is also caused to weeds which have up to now have only been controlled with total herbicides.

The mode of action of these compounds is unusual. Many are translocatable, i.e. they are absorbed by the plant and transported to other parts of it where they then deploy their action. The unusual feature of the compounds is that they do not only take the path through the vascular bundle in the ligneous part from the roots to the leaves, but can also be translocated through the sieve tubes in the bast part of the leaves back into the roots. Thus, for example, it is possible to damage perennial weeds to the very roots by surface treatment. Compared with other herbicides and growth regulators, the novel compounds of the formula I are effective even when used in very low rates of application.

The invention also relates to herbicidal and plant growth-regulating compositions which contain a novel compound of the formula I, and also to methods of controlling weeds pre- and postemergence and of inhibiting the growth of monocots and dicots, especially grasses, tropical cover crops and tobacco plant suckers.

The compounds of the formula I are used in unmodified form or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. The methods of application, such as spraying, atomising, dusting, scattering or pouring, are chosen in accordance with the intended objectives and the prevailing circumstances, just like the nature of the compositions.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali, alkaline earth or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali, alkaline earth or unsubstituted or substituted ammonium salts and contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminepolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenol-polyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one polyglycol ether or $C_8$-$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications: "McCutcheon's Detergents and Emulsifiers Annual", MC Publishing Corp., Ringwodd, N.J., 1979; Sisely and Wood, "Encyclopedia of Surface Active Agents", Chemical Publishing Co. Inc., New York, 1964.

The pesticidal formulations usually contain 0.1 to 95%, preferably 0.1 to 80%, of a compound of the formula I, 1 to 99.9% of a solid or liquid adjuvant, and 0 to 25%, preferably 0.1 to 25%, of a surfactant.

Preferred formulations are composed in particular of the following constituents (%=percentage by weight):

SOLUTIONS active ingredient: 1 to 30%, preferably 5 to 20%
solvent: 99 to 0%, preferably 95 to 0%
surfactants: 1 to 99%, preferably 0 to 95%

EMULSIFIABLE CONCENTRATES active ingredient: 1 to 20%, preferably 5 to 10%
surfactant: 5 to 30%, preferably 10 to 20%
liquid carrier: 50 to 94%, preferably 70 to 85%

DUSTS active ingredient: 0.1 to 10%, preferably 0.1 to 1%
solid carrier: 99.9 to 90%, preferably 99.9 to 99%

SUSPENSION CONCENTRATES active ingredient: 5 to 75%, preferably 10 to 50%
water: 94 to 25%, preferably 90 to 30%
surfactant: 1 to 40%, preferably 2 to 30%

WETTABLE POWDERS active ingredient: 0.5 to 90%, preferably 1 to 80%
surfactant: 0.5 to 20%, preferably 1 to 15%
solid carrier: 5 to 95%, preferably 15 to 90%

GRANULATES active ingredient: 0.5 to 30%, preferably 3 to 15%
solid carrier: 99.5 to 70%, preferably 97 to 85%.

Whereas commercial products will be preferably formulated as concentrates, the end user will normally employ dilute formulations. The formulations can be diluted to a concentration as low as 0.001%. The rates of application are normally 0.01 to 10 kg a.i./ha, preferably 0.025 to 5 kg a.i./ha.

The compositions can also contain further ingredients such as stabilisers, antifoams, viscosity regulators, binders, adhesives, as well as fertilisers or other active compounds, in order to attain special effects.

PREPARATORY EXAMPLES

Example 1

2-Hydroxyphenylsulfonamide 22.2 ml of boron tribromide are added dropwise, under nitrogen and at room temperature, over 15 minutes to a suspension of 39 g of 2-methoxyphenylsulfonamide in 210 ml of dry methylene chloride. The reaction mixture is then stirred for 1 hour at room temperature. After the mixture has been cooled to 0° C., 200 ml of methanol are added over 15 minutes and the clear solution is concentrated. The oily residue is taken up in ethyl acetate and the solution is washed twice with water, dried over sodium sulfate, and evaporated to dryness. The residue is triturated with petroleum ether, affording 25.1 g of 2-hydroxyphenylsulfonamide with a melting point of 136°–138° C.

The hydroxyphenylsulfonamides of the formula VIII listed in the following Table 1 are obtained in analogous manner:

TABLE 1

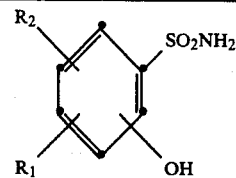

| $R_1$ | $R_2$ | Position of —OH | Physical data (°C.) |
|---|---|---|---|
| 5-CH(CH$_3$)$_2$ | H | 2 | m.p. 90–91° |
| 2-CH$_3$ | H | 5 | |
| 2-Cl | H | 5 | |
| 5-F | H | 2 | m.p. 141–142° |
| 5-Br | H | 2 | m.p. 169–70° |
| 5-NO$_2$ | H | 2 | m.p. 180–185° |
| 3-CH$_3$ | H | 2 | m.p. 133–134° |
| 2-CH$_3$ | H | 3 | |
| 3-Cl | H | 2 | |
| 6-CH$_3$ | H | 2 | |
| 3-OCH$_3$ | H | 2 | |
| 2-OCH$_3$ | H | 3 | |
| 3-CH$_3$ | 5-t-C$_4$H$_9$ | 2 | m.p. 134–137° |
| 6-OCH$_3$ | H | 2 | |
| 6-OH | H | 2 | |
| 5-OCH$_3$ | H | 2 | m.p. 119–20° |
| 2-OCH$_3$ | H | 5 | m.p. 213–15° |
| 5-CH$_3$ | H | 2 | m.p. 155–156° |
| 6-Cl | H | 2 | m.p. 190–91° |
| 3-NO$_2$ | H | 2 | |
| 3-COOCH$_3$ | H | 2 | |
| 5-COOCH$_3$ | H | 2 | m.p. 171–172° |
| 5-Cl | H | 2 | m.p. 176–179° |
| 5-NO$_2$ | 3-CF$_3$ | 2 | |
| 5-NO$_2$ | 3-Cl | 2 | |
| 5-CF$_3$ | 3-NO$_2$ | 2 | |
| 5-CH$_3$ | 3-CH$_3$ | 2 | |
| 5-Cl | 3-NO$_2$ | 2 | |
| 5-Cl | 3-Cl | 2 | m.p. 156–158° |
| 5-Br | 3-OCH$_3$ | 2 | |
| 5-Br | 2-OCH$_3$ | 3 | m.p. 194–197° |
| 3-OCH$_3$ | 5-COOCH$_3$ | 2 | |
| 2-OCH$_3$ | 5-COOCH$_3$ | 3 | |
| 5-CH$_3$ | 3-Br | 2 | |
| 5-Br | 3-NO$_2$ | 2 | |
| 5-Br | 3-COOCH$_3$ | 2 | |
| 5-COOCH$_3$ | 3-NO$_2$ | 2 | |
| 5-Cl | 3-Br | 2 | m.p. 247–249° |
| 3-NH$_2$ | H | 2 | |
| 5-NH$_2$ | H | 2 | |
| 5-COOC$_3$H$_7$(i) | 3-NO$_2$ | 2 | |
| 5-CON(CH$_3$)$_2$ | H | 2 | |
| 6-NO$_2$ | H | 2 | |
| 6-COOCH$_3$ | H | 2 | |

Example 2

2-Allyloxyphenylsulfonamide

A mixture of 3.5 g of 2-hydroxyphenylsulfonamide, 5.5 g of potassium carbonate and 1.7 ml of allyl bromide in 100 ml of methyl ethyl ketone is stirred, under nitrogen, for 1 hour at reflux temperature. The reaction mixture is cooled to room temperature, filtered, and evaporated to dryness. One recrystallisation from ethyl acetate yields 3.27 g of 2-allyloxyphenylsulfonamide with a melting point of 104°–105° C.

Sulfonamides of the formula II which can be obtained in analogous manner are listed in Table 2.

TABLE 2

$$\text{R}_1, \text{R}_2, \text{X-A substituted benzene with } SO_2-NH_2$$

| $R_1$ | $R_2$ | X | A | Position of —X—A | Physical data (°C.) |
|---|---|---|---|---|---|
| H | H | O | —CCl=CHCl | 2 | m.p. 147–149° |
| H | H | S | —CCl=CHCl | 2 | |
| H | H | SO | —CCl=CHCl | 2 | |
| H | H | $SO_2$ | —CCl=CHCl | 2 | |
| H | H | O | —CH=$CCl_2$ | 2 | |
| H | H | S | —CH=$CCl_2$ | 2 | |
| H | H | SO | —CH=$CCl_2$ | 2 | |
| H | H | $SO_2$ | —CH=$CCl_2$ | 2 | |
| H | H | O | —$CH_2CH$=$CH_2$ | 2 | m.p. 104–5° |
| H | H | S | —$CH_2CH$=$CH_2$ | 2 | |
| H | H | O | —$CH_2$—C($CH_3$)=$CH_2$ | 2 | m.p. 104–105° |
| H | H | S | —$CH_2$—C($CH_3$)=$CH_2$ | 2 | |
| H | H | O | —$(CH_2)_2$—CH=$CH_2$ | 2 | |
| H | H | O | —$(CH_2)_3$—CH=$CH_2$ | 2 | |
| H | H | O | —$CH_2$—CH=C($CH_3$)$_2$ | 2 | |
| H | H | S | —$CH_2$—CH=C($CH_3$)$_2$ | 2 | |
| H | H | O | —$CH_2$—CH=CH—$CH_3$ | 2 | m.p. 113–114° |
| H | H | S | —$CH_2$—CH=CH—$CH_3$ | 2 | |
| H | H | O | —CH($CH_3$)—CH=$CH_2$ | 2 | |
| H | H | S | —CH($CH_3$)—CH=$CH_2$ | 2 | |
| H | H | O | —$CH_2$—$OCH_3$ | 2 | decomp. from 121° |
| H | H | O | —$CH_2$—$OC_2H_5$ | 2 | |
| H | H | O | —$CH_2$—S—$CH_3$ | 2 | |
| H | H | O | —$CH_2CH_2$—$OCH_3$ | 2 | m.p. 110–112° |
| H | H | S | —$CH_2CH_2$—$OCH_3$ | 2 | |
| H | H | O | —$CH_2CH_2$—$OC_2H_5$ | 2 | |
| H | H | O | —$CH_2CH_2$—$SCH_3$ | 2 | |
| 6-Cl | H | O | —$CH_2CH$=$CH_2$ | 2 | m.p. 127–128° |
| 6-Cl | H | O | —$CH_2$—C($CH_3$)=$CH_2$ | 2 | |
| 6-Cl | H | O | —$CH_2$—CH=C($CH_3$)$_2$ | 2 | |
| 6-Cl | H | O | —$CH_2OCH_3$ | 2 | |
| 6-Cl | H | O | —$(CH_2)_2OCH_3$ | 2 | |
| 6-Cl | H | O | —$CH_2SCH_3$ | 2 | |

TABLE 2-continued

Structure: benzene ring with R₁, R₂, X—A substituents and —SO₂—NH₂ group

| R₁ | R₂ | X | A | Position of —X—A | Physical data (°C.) |
|---|---|---|---|---|---|
| 6-Cl | H | O | —(CH₂)₂SCH₃ | 2 | |
| 6-Cl | H | O | —CH₂—CH=CH—CH₃ | 2 | |
| 6-OCH₃ | H | O | —CH₂—CH=CH₂ | 2 | |
| 6-OCH₃ | H | O | —CH₂—C(CH₃)=CH₂ | 2 | |
| 6-OCH₃ | H | O | —(CH₂)₂—OC₂H₅ | 2 | |
| 6-OCH₃ | H | O | —CH₂—CH=C(CH₃)₂ | 2 | |
| 6-OCH₃ | H | O | —(CH₂)₂—CH=CH₂ | 2 | |
| 6-CH₃ | H | O | —CH₂—CH=CH₂ | 2 | |
| 6-CH₃ | H | O | —CH₂—C(CH₃)=CH₂ | 2 | |
| 6-CH₃ | H | O | —(CH₂)₂—OCH₃ | 2 | |
| 6-CH₃ | H | O | —CH₂SCH₃ | 2 | |
| H | H | O | —CH₂CH₂—OCH₂CH=CH₂ | 2 | |
| 6-NO₂ | H | O | —CH₂—CH=CH₂ | 2 | |
| 6-NO₂ | H | O | —CH₂—CH=CH—CH₃ | 2 | |
| 6-NO₂ | H | O | —CH₂—OCH₃ | 2 | |
| 6-NO₂ | H | O | —CH₂—CH₂—OC₂H₅ | 2 | |
| 6-NO₂ | H | O | —CH₂—C(CH₃)=CH₂ | 2 | |
| 6-COOCH₃ | H | O | —CH₂—CH=CH₂ | 2 | |
| 5-Cl | H | O | —CH₂—CH=CH₂ | 2 | m.p. 122° |
| 5-Cl | H | O | —CH₂—C(CH₃)=CH₂ | 2 | |
| 5-Br | H | O | —CH₂—C(CH₃)=CH₂ | 2 | |
| 5-Br | H | O | —CH₂—CH=CH₂ | 2 | m.p. 110–111° |
| 5-Br | H | O | —CH₂—OCH₃ | 2 | |
| 5-F | H | O | —CH₂—CH=CH₂ | 2 | m.p. 113–114° |
| 5-F | H | O | —CH₂—CH=C(CH₃)₂ | 2 | |
| 5-CH(CH₃)₂ | H | O | —CH₂—CH=C(CH₃)₂ | 2 | |
| 5-CH(CH₃)₂ | H | O | —CH₂—CH=CH₂ | 2 | oil |
| 5-CH(CH₃)₂ | H | O | —CH₂CH₂OCH₃ | 2 | |

TABLE 2-continued $$\text{R}_1\text{-}\underset{\underset{X-A}{|}}{\underset{R_2}{\bigcirc}}\text{-SO}_2\text{-NH}_2$$

| R₁ | R₂ | X | A | Position of —X—A | Physical data (°C.) |
|---|---|---|---|---|---|
| 5-CH₃ | H | O | —CH₂CH₂OCH₃ | 2 | |
| 5-CH₃ | H | O | —CH₂—CH=CH₂ | 2 | m.p. 139–140° |
| 5-CH₃ | H | O | —CH₂—CH=CH—CH₃ | 2 | |
| 5-NO₂ | H | O | —CH₂—CH=CH—CH₃ | 2 | |
| 5-NO₂ | H | O | —CH₂—S—CH₃ | 2 | |
| 5-NO₂ | H | O | —CH₂CH=CH₂ | 2 | m.p. 138–141° |
| 5-OCH₃ | H | O | —CH₂CH=CH₂ | 2 | m.p. 88–89° |
| 5-OCH₃ | H | O | —CH₂—C(CH₃)=CH₂ | 2 | |
| 5-OCH₃ | H | O | —CH₂CH=CH—CH₃ | 2 | |
| 5-OCH₃ | H | O | —CH₂OCH₃ | 2 | |
| 5-OCH₃ | H | O | —CH₂CH₂—SCH₃ | 2 | |
| 5-CON(CH₃)₂ | H | O | —CH₂—CH=CH₂ | 2 | |
| 5-CON(CH₃)₂ | H | O | —CH₂—C(CH₃)=CH₂ | 2 | |
| 5-COOCH₃ | H | O | —CH₂—CH=CH₂ | 2 | |
| 5-COOCH₃ | H | O | —CH₂—C(CH₃)=CH₂ | 2 | |
| 5-COOCH₃ | H | O | —CH₂—OC₂H₅ | 2 | |
| 5-NO₂ | 3-CF₃ | O | —CH₂—CH=CH₂ | 2 | |
| 5-NO₂ | 3-Cl | O | —CH₂—CH=CH₂ | 2 | |
| 5-NO₂ | 3-Cl | O | —CH₂—C(CH₃)=CH₂ | 2 | |
| 5-CF₃ | 3-NO₂ | O | —CH₂—CH=CH₂ | 2 | |
| 5-CH₃ | 3-CH₃ | O | —CH₂—CH=CH₂ | 2 | |
| 5-CH₃ | 3-CH₃ | O | —CH₂—CH=CH—CH₃ | 2 | |
| 5-Cl | 3-NO₂ | O | —CH₂—CH=CH—CH₃ | 2 | |
| 5-Cl | 3-Cl | O | —CH₂—CH=CH₂ | 2 | m.p. 161–162° |
| 5-Cl | 3-Cl | O | —CH₂—CH₂—OCH₃ | 2 | |
| 5-Cl | 3-Cl | O | —CH₂—OCH₃ | 2 | |
| 5-Br | 3-OCH₃ | O | —CH₂—CH=CH₂ | 2 | |
| 5-Br | 2-OCH₃ | O | —CH₂—CH=CH₂ | 3 | resin |
| 3-OCH₃ | 5-COOCH₃ | O | —CH₂—CH=CH₂ | 2 | |
| 2-OCH₃ | 5-COOCH₃ | O | —CH₂—C(CH₃)=CH₂ | 3 | |
| 5-CH₃ | 3-Br | O | —CH₂—OCH₃ | 2 | |
| 5-Br | 3-NO₂ | O | —CH₂CH=CH₂ | 2 | |
| 5-Cl | 3-Br | O | —CH₂CH=CH₂ | 2 | m.p. 179° |
| 5-Cl | 3-Br | O | —CH₂—C(CH₃)=CH₂ | 2 | |
| 5-Cl | 3-Br | O | —CH₂—CH₂—OCH₃ | 3 | |
| H | H | SO | —CH₂—CH=CH₂ | 2 | |
| H | H | SO₂ | —CH₂—CH=CH₂ | 2 | |
| H | H | SO | —CH₂—CH=CH—CH₃ | 2 | |
| H | H | SO₂ | —CH₂—CH=CH—CH₃ | 2 | |
| H | H | O | —CH₂—SO—CH₃ | 2 | |

TABLE 2-continued $$\text{structure: benzene ring with } R_1, R_2, X-A \text{ substituents and } SO_2-NH_2$$

| R₁ | R₂ | X | A | Position of —X—A | Physical data (°C.) |
|---|---|---|---|---|---|
| H | H | O | —CH₂—SO₂—CH₃ | 2 | |
| H | H | O | —CH₂—CH₂—SO—CH₃ | 2 | |
| H | H | O | —CH₂—CH₂—SO₂—CH₃ | 2 | |
| H | H | O | —CH₂—C(Cl)=CH₂ | 2 | |
| H | H | O | —CH₂—C(Cl)=CH—Cl | 2 | |
| H | H | O | —CH₂—CH=C(Cl)—CH₃ | 2 | |
| H | H | O | —CH₂—CH=C(Cl)(Cl) | 2 | |
| 5-CH₃ | H | O | —CH₂—C(Cl)=CH₂ | 2 | |
| 5-NO₂ | H | O | —CH₂—C(Cl)=CH—Cl | 2 | |
| 5-Br | H | O | —CH₂—C(Cl)—CH₂ | 2 | |
| 5-Cl | H | O | —CH₂—CH=C(Cl)(Cl) | 2 | |
| 5-CH(CH₃)₂ | H | O | —CH₂—CH=C(Cl)—CH₃ | 2 | |
| 3-CH₃ | H | O | —CH₂—C(Cl)=CH | 2 | |
| 6-CH₃ | H | O | —CH₂—C(Cl)—CH₂ | 2 | |
| 6-OCH₃ | H | O | —CH₂—C(Cl)=CH—Cl | 2 | |
| 5-OCH₃ | H | O | —CH₂—CH=C(Cl)(Cl) | 2 | |
| 6-Cl | H | O | —CH₂—C(Cl)=CH₂ | 2 | |
| 3-NO₂ | H | O | —CH₂—CH=C(Cl)—CH₃ | 2 | |
| 3-CH₃ | H | O | —CH₂—CH=CH₃ | 2 | m.p. 114–116° |
| 3-NO₂ | H | O | —CH₂—CH=CH₃ | 2 | |
| 3-Cl | H | O | —CH₂—CH=CH₃ | 2 | |

TABLE 2-continued

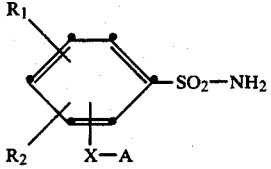

| $R_1$ | $R_2$ | X | A | Position of —X—A | Physical data (°C.) |
|---|---|---|---|---|---|
| 3-Cl | H | O | —CH$_2$—CH=CH—CH$_3$ | 2 | |
| 3-Cl | H | O | —CH—C(CH$_3$)=CH$_2$ | 2 | |
| 3-OCH$_3$ | H | O | —CH—C(CH$_3$)=CH$_2$ | 2 | |
| 3-OCH$_3$ | H | O | —CH$_2$—CH=CH$_2$ | 2 | |
| 2-OCH$_3$ | H | O | —CH$_2$—CH=CH$_2$ | 5 | m.p. 113–114° |

Example 3

(a) N-(2-Allyloxyphenylsulfonyl)phenylcarbamate 2.76 g of 2-allyloxyphenylsulfonamide in 20 ml of dimethyl formamide are added dropwise, under nitrogen, over 5 minutes and at a maximum temperature of 20° C., to a suspension of 0.56 g of sodium hydride (55%) in 5 ml of absolute dimethyl formamide, and the suspension is stirred for about 10 minutes before the dropwise addition of 2.91 g of diphenyl carbonate in 20 ml of dimethyl formamide. The reaction mixture is stirred for a further ½ hour and then taken up in a mixture of 80 ml of ethyl acetate, 80 g of ice and 12.3 ml of 2N hydrochloric acid. The organic phase is washed twice with ice-water, dried over sodium sulfate and evaporated to dryness. Crystallisation from ether/petroleum ether (1:1) yields 3.5 g of N-(2-allyloxyphenylsulfonyl)phenylcarbamate with a melting point of 140°–141° C.

(b) N-(2-Allyloxyphenylsulfonyl)-N'-(4-methoxy-6-methyl-1,3,5-triazin-2-yl)urea

A mixture of 3.33 g of N-(2-allyloxyphenylsulfonyl)-phenylcarbamate and 1.4 g of 2-amino-4-methoxy-6-methyl-1,3,5-triazine in 30 ml of absolute dioxane is heated to reflux for ½ hour, then cooled to 20° C., filtered, evaporated to dryness, and the residue is crystallised from ether. Recrystallisation from ethyl acetate/-petroleum ether (1:1) yields 2 g of N-(2-allyloxyphenylsulfonyl)-N'-(4-methoxy-6-methyl-1,3,5-triazin-2-yl)urea with a melting point of 146°–147° C.

The compounds of formula I listed in Table 3 are obtained in analogous manner:

TABLE 3

| No. | A | $R_1$ | $R_3$ | $R_4$ | X | E | Physical data (°C.) |
|---|---|---|---|---|---|---|---|
| 1 | —CH$_2$—CH=CH$_2$ | 6-Cl | CH$_3$ | OCH$_3$ | O | N | |
| 2 | —CH$_2$—CH=CH$_2$ | 6-Cl | CH$_3$ | OCH$_3$ | O | CH | |
| 3 | —CH$_2$—CH=CH$_2$ | 6-Cl | C$_2$H$_5$ | OCH$_3$ | O | N | |
| 4 | —CH$_2$—CH=CH$_2$ | 6-Cl | OCH$_3$ | OCH$_3$ | O | CH | |
| 5 | —CH$_2$—CH=CH$_2$ | 6-Cl | OCH$_3$ | OCH$_3$ | O | N | |
| 6 | —CH$_2$—C(CH$_3$)=CH$_2$ | 6-Cl | CH$_3$ | OCH$_3$ | O | N | |
| 7 | —CH$_2$—C(CH$_3$)=CH$_2$ | 6-Cl | CH$_3$ | OCH$_3$ | O | CH | |
| 8 | —CH$_2$—C(CH$_3$)=CH$_2$ | 6-Cl | C$_2$H$_5$ | OCH$_3$ | O | N | |
| 9 | —CH$_2$—C(CH$_3$)=CH$_2$ | 6-Cl | OCH$_3$ | OCH$_3$ | O | N | |

TABLE 3-continued

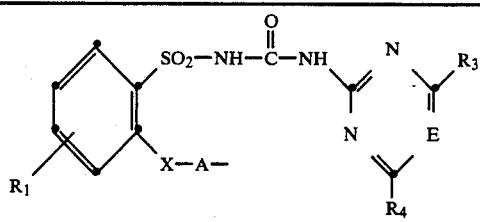

| No. | A | $R_1$ | $R_3$ | $R_4$ | X | E | Physical data (°C.) |
|---|---|---|---|---|---|---|---|
| 10 | −CH$_2$−C(CH$_3$)=CH$_2$ | 6-Cl | OCH$_3$ | OCH$_3$ | O | CH | |
| 11 | −CH$_2$−CH=CH−CH$_3$ | 6-Cl | OCH$_3$ | OCH$_3$ | O | CH | |
| 12 | −CH$_2$−CH=CH−CH$_3$ | 6-Cl | OCH$_3$ | OCH$_3$ | O | N | |
| 13 | −CH$_2$−CH=CH−CH$_3$ | 6-Cl | OCH$_3$ | CH$_3$ | O | N | |
| 14 | −CH$_2$−CH=CH−CH$_3$ | 6-Cl | OCH$_3$ | CH$_3$ | O | CH | |
| 15 | −CH$_2$CH=C(CH$_3$)$_2$ | 6-Cl | CH$_3$ | OCH$_3$ | O | N | |
| 16 | −CH$_2$−CH=C(CH$_3$)$_2$ | 6-Cl | CH$_3$ | OCH$_3$ | O | CH | |
| 17 | −CH$_2$−OCH$_3$ | 6-Cl | CH$_3$ | OCH$_3$ | O | CH | |
| 18 | −CH$_2$−OCH$_3$ | 6-Cl | CH$_3$ | OCH$_3$ | O | N | |
| 19 | −CH$_2$−OCH$_3$ | 6-Cl | C$_2$H$_5$ | OCH$_3$ | O | N | |
| 20 | −(CH$_2$)$_2$−OCH$_3$ | 6-Cl | CH$_3$ | OCH$_3$ | O | N | |
| 21 | −(CH$_2$)$_2$−OCH$_3$ | 6-Cl | CH$_3$ | OCH$_3$ | O | CH | |
| 22 | −CH$_2$−SCH$_2$ | 6-Cl | CH$_3$ | OCH$_3$ | O | CH | |
| 23 | −CH$_2$−SCH$_2$ | 6-Cl | CH$_3$ | OCH$_3$ | O | N | |
| 24 | −(CH$_2$)$_2$−SCH$_2$ | 6-Cl | CH$_3$ | OCH$_3$ | O | N | |
| 25 | −(CH$_2$)$_2$−SCH$_2$ | 6-Cl | CH$_3$ | OCH$_3$ | O | CH | |
| 26 | −CH$_2$CH=CH$_2$ | 6-OCH$_3$ | CH$_3$ | OCH$_3$ | O | CH | |
| 27 | −CH$_2$CH=CH$_2$ | 6-OCH$_3$ | CH$_3$ | OCH$_3$ | O | N | |
| 28 | −CH$_2$CH=CH$_2$ | 6-OCH$_3$ | C$_2$H$_5$ | OCH$_3$ | O | N | |
| 29 | −CH$_2$CH=CH$_2$ | 6-OCH$_3$ | OCH$_3$ | OCH$_3$ | O | N | |
| 30 | −CH$_2$CH=CH$_2$ | 6-OCH$_3$ | OCH$_3$ | OCH$_3$ | O | CH | |
| 31 | −CH$_2$−C(CH$_3$)=CH$_2$ | 6-OCH$_3$ | OCH$_3$ | OCH$_3$ | O | CH | |
| 32 | −CH$_2$−C(CH$_3$)=CH$_2$ | 6-OCH$_3$ | CH$_3$ | OCH$_3$ | O | N | |
| 33 | −CH$_2$−C(CH$_3$)=CH$_2$ | 6-OCH$_3$ | CH$_3$ | OCH$_3$ | O | CH | |
| 34 | −(CH$_2$)$_2$−OC$_2$H$_5$ | 6-OCH$_3$ | CH$_3$ | OCH$_3$ | O | CH | |
| 35 | −(CH$_2$)$_2$−OC$_2$H$_5$ | 6-OCH$_3$ | CH$_3$ | OCH$_3$ | O | N | |
| 36 | −CH$_2$−CH=C(CH$_3$)$_2$ | 6-Cl | CH$_3$ | OCH$_3$ | O | N | |
| 37 | −CH$_2$−CH=C(CH$_3$)$_2$ | 6-Cl | CH$_3$ | OCH$_3$ | O | CH | |
| 38 | −CH(Cl)−C=CH$_2$ | 6-OCH$_3$ | CH$_3$ | OCH$_3$ | O | N | |
| 39 | −CH(Cl)−C=CH$_2$ | 6-OCH$_3$ | CH$_3$ | OCH$_3$ | O | CH | |

TABLE 3-continued

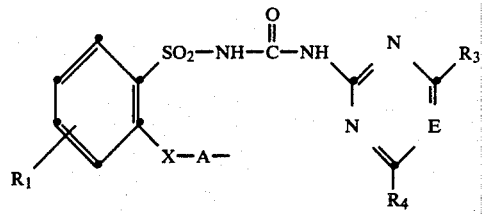

| No. | A | $R_1$ | $R_3$ | $R_4$ | X | E | Physical data (°C.) |
|---|---|---|---|---|---|---|---|
| 40 | —CH—C(Cl)=CH$_2$ | 6-Cl | CH$_3$ | OCH$_3$ | O | CH | m.p. 163–164° |
| 41 | —CH—C(Cl)=CH$_2$ | 6-Cl | CH$_3$ | OCH$_3$ | O | N | m.p. 142–145° |
| 42 | —CH$_2$—CH=CH$_2$ | 6-CH$_3$ | CH$_3$ | OCH$_3$ | O | N | |
| 43 | —CH$_2$—CH=CH$_2$ | 6-CH$_3$ | CH$_3$ | OCH$_3$ | O | CH | |
| 44 | —CH$_2$—CH=CH$_2$ | 6-CH$_3$ | OCH$_3$ | OCH$_3$ | O | CH | |
| 45 | —CH$_2$—CH=CH$_2$ | 6-CH$_3$ | OCH$_3$ | OCH$_3$ | O | N | |
| 46 | —CH$_2$—C(CH$_3$)=CH$_2$ | 6-CH$_3$ | CH$_3$ | OCH$_3$ | O | N | |
| 47 | —CH$_2$—C(CH$_3$)=CH$_2$ | 6-CH$_3$ | CH$_3$ | OCH$_3$ | O | CH | |
| 48 | —CH$_2$—C(CH$_3$)=CH$_2$ | 6-CH$_3$ | OCH$_3$ | OCH$_3$ | O | N | |
| 49 | —CH$_2$—C(CH$_3$)=CH$_2$ | 6-CH$_3$ | OCH$_3$ | OCH$_3$ | O | CH | |
| 50 | —CH$_2$—OCH$_3$ | 6-CH$_3$ | OCH$_3$ | OCH$_3$ | O | CH | |
| 51 | —CH$_2$—OCH$_3$ | 6-CH$_3$ | OCH$_3$ | CH$_3$ | O | CH | |
| 52 | —CH$_2$—OCH$_3$ | 6-CH$_3$ | OCH$_3$ | CH$_3$ | O | N | |
| 53 | —(CH$_2$)$_2$—CH=CH$_2$ | 6-OCH$_3$ | OCH$_3$ | CH$_3$ | O | N | |
| 54 | —(CH$_2$)$_2$—CH=CH$_2$ | 6-OCH$_3$ | OCH$_3$ | CH$_3$ | O | CH | |
| 55 | —CH$_2$—SCH$_3$ | 6-CH$_3$ | OCH$_3$ | CH$_3$ | O | CH | |
| 56 | —CH$_2$—SCH$_3$ | 6-CH$_3$ | OCH$_3$ | CH$_3$ | O | N | |
| 57 | —CH$_2$—CH=CH$_2$ | 6-NO$_2$ | CH$_3$ | OCH$_3$ | O | N | |
| 58 | —CH$_2$—CH=CH$_2$ | 6-NO$_2$ | CH$_3$ | OCH$_3$ | O | CH | |
| 59 | —CH$_2$—CH=CH$_2$ | 6-NO$_2$ | OCH$_3$ | OCH$_3$ | O | CH | |
| 60 | —CH$_2$—CH=CH$_2$ | 6-NO$_2$ | OCH$_3$ | OCH$_3$ | O | N | |
| 61 | —CH$_2$—CH=CH—CH$_3$ | 6-NO$_2$ | OCH$_3$ | OCH$_3$ | O | N | |
| 62 | —CH$_2$—CH=CH—CH$_3$ | 6-NO$_2$ | OCH$_3$ | OCH$_3$ | O | CH | |
| 63 | —CH$_2$—CH=CH—CH$_3$ | 6-NO$_2$ | OCH$_3$ | CH$_3$ | O | CH | |
| 64 | —CH$_2$—CH=CH—CH$_3$ | 6-NO$_2$ | OCH$_3$ | CH$_3$ | O | N | |
| 65 | —CH$_2$—OCH$_3$ | 6-NO$_2$ | OCH$_3$ | CH$_3$ | O | N | |
| 66 | —CH$_2$—OCH$_3$ | 6-NO$_2$ | OCH$_3$ | CH$_3$ | O | CH | |
| 67 | —CH$_2$—CH$_2$—OC$_2$H$_5$ | 6-NO$_2$ | OCH$_3$ | CH$_3$ | O | CH | |
| 68 | —CH$_2$—CH$_2$—OC$_2$H$_5$ | 6-NO$_2$ | OCH$_3$ | CH$_3$ | O | N | |
| 69 | —CH$_2$—C(CH$_3$)=CH$_2$ | 6-NO$_2$ | OCH$_3$ | CH$_3$ | O | N | |
| 70 | —CH$_2$—C(CH$_3$)=CH$_2$ | 6-NO$_2$ | OCH$_3$ | CH$_3$ | O | CH | |
| 71 | —CH$_2$—CH=CH$_2$ | 6-COOCH$_3$ | OCH$_3$ | CH$_3$ | O | CH | |
| 72 | —CH$_2$—CH=CH$_2$ | 6-COOCH$_3$ | OCH$_3$ | CH$_3$ | O | N | |
| 73 | —CH$_2$—CH=CH$_2$ | 6-COOCH$_3$ | OCH$_3$ | OCH$_3$ | O | N | |
| 74 | —CH$_2$—CH=CH$_2$ | 6-COOCH$_3$ | OCH$_3$ | OCH$_3$ | O | CH | |
| 75 | —CH$_2$CH=CH$_2$ | 5-Cl | CH$_3$ | OCH$_3$ | O | N | |
| 76 | —CH$_2$CH=CH$_2$ | 5-Cl | CH$_3$ | OCH$_3$ | O | CH | |
| 77 | —CH$_2$CH=CH$_2$ | 5-Cl | OCH$_3$ | OCH$_3$ | O | N | |
| 78 | —CH$_2$CH=CH$_2$ | 5-Cl | OCH$_3$ | OCH$_3$ | O | N | |
| 79 | —CH$_2$CH=CH$_2$ | 5-Cl | C$_2$H$_5$ | OCH$_3$ | O | N | |

TABLE 3-continued

Structure:

$$\text{Ar-SO}_2\text{-NH-C(O)-NH-[pyrimidine/triazine with } R_3, R_4, E\text{]}$$

where Ar = phenyl with $R_1$ and $X-A-$ substituents.

| No. | A | $R_1$ | $R_3$ | $R_4$ | X | E | Physical data (°C.) |
|---|---|---|---|---|---|---|---|
| 80 | $-CH_2-C(CH_3)=CH_2$ | 5-Cl | $CH_3$ | $OCH_3$ | O | N | |
| 81 | $-CH_2-C(CH_3)=CH_2$ | 5-Cl | $CH_3$ | $OCH_3$ | O | CH | |
| 82 | $-CH_2CH=CH_2$ | 5-Br | $CH_3$ | $OCH_3$ | O | CH | |
| 83 | $-CH_2CH=CH_2$ | 5-Br | $CH_3$ | $OCH_3$ | O | N | m.p. 190–191° |
| 84 | $-CH_2CH=CH_2$ | 5-Br | $C_2H_5$ | $CH_3$ | O | N | |
| 85 | $-CH(CH_3)-C=CH_2$ (with CH3) | 5-Br | $CH_3$ | $OCH_3$ | O | N | |
| 86 | $-CH(CH_3)-C=CH_2$ (with CH3) | 5-Br | $OCH_3$ | $OCH_3$ | O | N | |
| 87 | $-CH(CH_3)-C=CH_2$ (with CH3) | 5-Br | $CH_3$ | $OCH_3$ | O | CH | |
| 88 | $-CH_2-OCH_3$ | 5-Br | $CH_3$ | $OCH_3$ | O | CH | |
| 89 | $-CH_2-OCH_3$ | 5-Br | $CH_3$ | $OCH_3$ | O | N | |
| 90 | $-CH_2-CH=CH_2$ | 5-F | $CH_3$ | $OCH_3$ | O | N | m.p. 159–161° |
| 91 | $-CH_2-CH=CH_2$ | 5-F | $CH_3$ | $OCH_3$ | O | CH | m.p. 200–201° |
| 92 | $-CH_2-CH=CH_2$ | 5-F | $OCH_3$ | $C_2H_5$ | O | N | |
| 93 | $-CH_2-CH=CH_2$ | 5-F | $OCH_3$ | $OCH_3$ | O | CH | m.p. 162–164° |
| 94 | $-CH_2-CH=C(CH_3)_2$ | 5-F | $CH_3$ | $OCH_3$ | O | N | |
| 95 | $-CH_2-CH=C(CH_3)_2$ | 5-F | $CH_3$ | $OCH_3$ | O | CH | |
| 96 | $-CH_2-C(CH_3)=CH_2$ | 5-F | $CH_3$ | $OCH_3$ | O | CH | |
| 97 | $-CH_2-C(CH_3)=CH_2$ | 5-F | $CH_3$ | $OCH_3$ | O | N | |
| 98 | $-CH_2-C(CH_3)=CH_2$ | 5-CH(CH$_3$)$_2$ | $CH_3$ | $OCH_3$ | O | N | |
| 99 | $-CH_2-C(CH_3)=CH_2$ | 5-CH(CH$_3$)$_2$ | $CH_3$ | $OCH_3$ | O | CH | |
| 100 | $-CH_2-CH=C(CH_3)_2$ | 5-CH(CH$_3$)$_2$ | $CH_3$ | $OCH_3$ | O | CH | |

TABLE 3-continued

Structure:

$$\text{Ar}(R_1)(X-A-)-SO_2-NH-C(=O)-NH-\text{[heterocycle with N, R_3, R_4, E]}$$

| No. | A | R₁ | R₃ | R₄ | X | E | Physical data (°C.) |
|---|---|---|---|---|---|---|---|
| 101 | −CH₂−CH=C(CH₃)(CH₃) | 5-CH(CH₃)(CH₃) | CH₃ | OCH₃ | O | N | |
| 102 | −CH₂−CH=CH₂ | 5-CH(CH₃)(CH₃) | CH₃ | OCH₃ | O | N | m.p. 259–260° |
| 103 | −CH₂−CH=CH₂ | 5-CH(CH₃)(CH₃) | CH₃ | OCH₃ | O | CH | m.p. 139–140° |
| 104 | −CH₂−CH=CH₂ | 5-CH(CH₃)(CH₃) | C₂H₅ | OCH₃ | O | N | |
| 105 | −CH₂−CH=CH₂ | 5-CH(CH₃)(CH₃) | OCH₃ | OCH₃ | O | N | m.p. 219–220° |
| 106 | −CH₂−CH₂−OCH₃ | 5-CH(CH₃)(CH₃) | CH₃ | OCH₃ | O | N | |
| 107 | −CH₂−CH₂−OCH₃ | 5-CH(CH₃)(CH₃) | CH₃ | OCH₃ | O | CH | |
| 108 | −CH₂−CH₂−OCH₃ | 5-CH₃ | CH₃ | OCH₃ | O | CH | |
| 109 | −CH₂−CH₂−OCH₃ | 5-CH₃ | CH₃ | OCH₃ | O | N | |
| 110 | −CH₂−CH₂−OCH₃ | 5-CH₃ | CH₃ | Cl | O | CH | |
| 111 | −CH₂−CH₂−OCH₃ | 5-CH₃ | OCH₃ | Cl | O | CH | |
| 112 | −CH₂−CH=CH₂ | 5-CH₃ | CH₃ | OCH₃ | O | N | m.p. 158–162° |
| 113 | −CH₂−CH=CH₂ | 5-CH₃ | CH₃ | OCH₃ | O | N | |
| 114 | −CH₂−CH=CH₂ | 5-CH₃ | C₂H₅ | OCH₃ | O | N | |
| 115 | −CH₂−CH=CH₂ | 5-CH₃ | OCH₃ | OCH₃ | O | N | m.p. 160–165° |
| 116 | −CH₂−CH=CH₂ | 5-CH₃ | OCH₃ | OCH₃ | O | CH | |
| 117 | −CH₂−CH=CH−CH₃ | 5-CH₃ | OCH₃ | OCH₃ | O | CH | |
| 118 | −CH₂−CH=CH−CH₃ | 5-CH₃ | CH₃ | OCH₃ | O | CH | m.p. 179–182° |
| 119 | −CH₂−CH=CH−CH₃ | 5-CH₃ | CH₃ | OCH₃ | O | N | |
| 120 | −CH₂−CH=CH−CH₃ | 5-NO₂ | CH₃ | OCH₃ | O | N | |
| 121 | −CH₂−CH=CH−CH₃ | 5-NO₂ | CH₃ | OCH₃ | O | CH | |
| 122 | −CH₂−CH=CH−CH₃ | 5-NO₂ | C₂H₅ | OCH₃ | O | N | |
| 123 | −CH₂−CH=CH−CH₃ | 5-NO₂ | OCH₃ | OCH₃ | O | N | |
| 124 | −CH₂−CH=CH₂ | 5-NO₂ | OCH₃ | OCH₃ | O | N | |
| 125 | −CH₂−CH=CH₂ | 5-NO₂ | CH₃ | OCH₃ | O | N | |
| 126 | −CH₂−CH=CH₂ | 5-NO₂ | CH₃ | OCH₃ | O | CH | |
| 127 | −CH₂−SCH₃ | 5-NO₂ | CH₃ | OCH₃ | O | CH | |
| 128 | −CH₂−SCH₃ | 5-NO₂ | CH₃ | OCH₃ | O | N | |
| 129 | −CH₂−SCH₃ | 5-NO₂ | OCH₃ | OCH₃ | O | N | |
| 130 | −CH₂−SCH₃ | 5-NO₂ | OCH₃ | OCH₃ | O | CH | |
| 131 | −CH₂−CH=CH₃ | 5-OCH₃ | CH₃ | OCH₃ | O | N | m.p. 142–143° |
| 132 | −CH₂−CH=CH₃ | 5-OCH₃ | CH₃ | OCH₃ | O | CH | m.p. 138–139° |
| 133 | −CH₂−CH=CH₃ | 5-OCH₃ | OCH₃ | OCH₃ | O | CH | |
| 134 | −CH₂−CH=CH₃ | 5-OCH₃ | OCH₃ | OCH₃ | O | N | |
| 135 | −CH₂−CH=CH₃ | 5-OCH₃ | OCH₃ | C₂H₅ | O | N | |

TABLE 3-continued

Structure: benzene ring with SO₂—NH—C(=O)—NH— linked to heterocycle with N, E, R₃, R₄ substituents; benzene has R₁ and X—A— substituents.

| No. | A | R₁ | R₃ | R₄ | X | E | Physical data (°C.) |
|---|---|---|---|---|---|---|---|
| 136 | —CH₂—C(CH₃)=CH₂ | 5-OCH₃ | OCH₃ | CH₃ | O | N | |
| 137 | —CH₂—C(CH₃)=CH₂ | 5-OCH₃ | OCH₃ | CH₃ | O | CH | |
| 138 | —CH₂—C(CH₃)=CH₂ | 5-OCH₃ | OCH₃ | OCH₃ | O | N | |
| 139 | —CH₂—CH=CH—CH₃ | 5-OCH₃ | OCH₃ | CH₃ | O | N | |
| 140 | —CH₂—CH=CH—CH₃ | 5-OCH₃ | OCH₃ | CH₃ | O | CH | |
| 141 | —CH₂—CH=CH—CH₃ | 5-OCH₃ | OCH₃ | OCH₃ | O | CH | |
| 142 | —CH₂—CH=CH—CH₃ | 5-OCH₃ | OCH₃ | OCH₃ | O | N | |
| 143 | —CH₂—OCH₃ | 5-OCH₃ | OCH₃ | OCH₃ | O | N | |
| 144 | —CH₂—OCH₃ | 5-OCH₃ | CH₃ | OCH₃ | O | N | |
| 145 | —CH₂—OCH₃ | 5-OCH₃ | CH₃ | OCH₃ | O | CH | |
| 146 | —CH₂—OCH₃ | 5-OCH₃ | C₂H₅ | OCH₃ | O | N | |
| 147 | —CH₂—CH₂—SCH₃ | 5-OCH₃ | CH₃ | OCH₃ | O | N | |
| 148 | —CH₂—CH₂—SCH₃ | 5-OCH₃ | CH₃ | OCH₃ | O | CH | |
| 149 | —CH₂—CH₂—SCH₃ | 5-OCH₃ | OCH₃ | OCH₃ | O | N | |
| 150 | —CH₂—CH=CH₂ | 5-CON(CH₃)₂ | CH₃ | OCH₃ | O | N | |
| 151 | —CH₂—CH=CH₂ | 5-CON(CH₃)₂ | CH₃ | OCH₃ | O | CH | |
| 152 | —CH₂—C(CH₃)=CH₂ | 5-CON(CH₃)₂ | CH₃ | OCH₃ | O | N | |
| 153 | —CH₂—C(CH₃)=CH₂ | 5-CON(CH₃)₂ | CH₃ | OCH₃ | O | CH | |
| 154 | —CH₂—C(CH₃)=CH₂ | 5-COOCH₃ | CH₃ | OCH₃ | O | CH | |
| 155 | —CH₂—C(CH₃)=CH₂ | 5-COOCH₃ | CH₃ | OCH₃ | O | N | |
| 156 | —CH₂—CH=CH₂ | 5-COOCH₃ | CH₃ | OCH₃ | O | N | |
| 157 | —CH₂—CH=CH₂ | 5-COOCH₃ | CH₃ | OCH₃ | O | CH | |
| 158 | —CH₂—CH=CH₂ | 5-COOCH₃ | OCH₃ | OCH₃ | O | N | |
| 159 | —CH₂—CH=CH₂ | 5-COOCH₃ | OCH₃ | OCH₃ | O | CH | |
| 160 | —CH₂—OC₂H₅ | 5-COOCH₃ | OCH₃ | CH₃ | O | N | |
| 161 | —CH₂—OC₂H₅ | 5-COOCH₃ | OCH₃ | CH₃ | O | N | |
| 162 | —CH₂—C(Cl)=CH₂ | 5-CH₃ | OCH₃ | CH₃ | O | N | |
| 163 | —CH₂—C(Cl)=CH₂ | 5-CH₃ | OCH₃ | CH₃ | O | CH | |

TABLE 3-continued

[Structure: aryl ring with SO₂—NH—C(=O)—NH— linked to a heterocycle containing N, N, E, with R₃ and R₄ substituents; aryl ring bears R₁ and X—A—]

| No. | A | R₁ | R₃ | R₄ | X | E | Physical data (°C.) |
|-----|---|----|----|----|---|---|---------------------|
| 164 | —CH₂—C(Cl)=CH—Cl | 5-NO₂ | OCH₃ | CH₃ | O | CH | |
| 165 | —CH₂—C(Cl)=CH—Cl | 5-NO₂ | OCH₃ | CH₃ | O | N | |
| 166 | —CH₂—C(Cl)=CH—Cl | 5-Br | OCH₃ | CH₃ | O | N | |
| 167 | —CH₂—C(Cl)=CH—Cl | 5-Br | OCH₃ | CH₃ | O | CH | |
| 168 | —CH₂—C(Cl)=CH—Cl | 5-Cl | OCH₃ | CH₃ | O | N | |
| 169 | —CH₂—C(Cl)=CH₂ | 5-Cl | CH₃ | OCH₃ | O | CH | |
| 170 | —CH₂—CH=C(Cl)(CH₃) | 5-Cl | CH₃ | OCH₃ | O | N | |
| 171 | —CH₂—CH=C(Cl)(CH₃) | 5-Cl | CH₃ | OCH₃ | O | CH | |
| 172 | —CH₂—CH=C(Cl)(Cl) | 5-CH(CH₃)₂ | CH₃ | OCH₃ | O | CH | |
| 173 | —CH₂—CH=C(Cl)(Cl) | 5-CH(CH₃)₂ | CH₃ | OCH₃ | O | N | |
| 174 | —CH₂—C(Cl)=CH₂ | 3-CH₃ | CH₃ | OCH₃ | O | N | |
| 175 | —CH₂—C(Cl)=CH₂ | 3-CH₃ | CH₃ | OCH₃ | O | CH | |
| 176 | —CH₂—C(Cl)=CH₂ | 6-CH₃ | CH₃ | OCH₃ | O | N | |
| 177 | —CH₂—C(Cl)=CH₂ | 6-CH₃ | CH₃ | OCH₃ | O | CH | |
| 178 | —CH₂—C(Cl)=CH—Cl | 6-OCH₃ | CH₃ | OCH₃ | O | CH | |
| 179 | —CH₂—C(Cl)=CH—Cl | 6-OCH₃ | CH₃ | OCH₃ | O | N | |

TABLE 3-continued

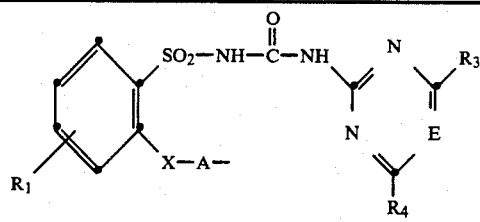

| No. | A | $R_1$ | $R_3$ | $R_4$ | X | E | Physical data (°C.) |
|---|---|---|---|---|---|---|---|
| 180 | —CH$_2$—CH=C(Cl)(Cl) | 5-OCH$_3$ | CH$_3$ | OCH$_3$ | O | N | |
| 181 | —CH$_2$—CH=C(Cl)(Cl) | 5-OCH$_3$ | CH$_3$ | OCH$_3$ | O | CH | |
| 182 | —CH$_2$—C(Cl)=CH$_2$ | 6-Cl | CH$_3$ | OCH$_3$ | O | N | |
| 183 | —CH$_2$—C(Cl)=CH$_2$ | 6-Cl | CH$_3$ | OCH$_3$ | O | CH | |
| 184 | —CH$_2$—CH=CH$_2$ | 3-NO$_2$ | CH$_3$ | OCH$_3$ | O | CH | |
| 185 | —CH$_2$—CH=CH$_2$ | 3-NO$_2$ | CH$_3$ | OCH$_3$ | O | N | |
| 186 | —CH$_2$—CH=CH$_2$ | 3-NO$_2$ | C$_2$H$_5$ | OCH$_3$ | O | N | |
| 187 | —CH$_2$—CH=CH$_2$ | 3-NO$_2$ | OCH$_3$ | OCH$_3$ | O | N | |
| 188 | —CH$_2$—C(CH$_3$)=CH$_2$ | 3-NO$_2$ | CH$_3$ | OCH$_3$ | O | N | |
| 189 | —CH$_2$—C(CH$_3$)=CH$_2$ | 3-NO$_2$ | CH$_3$ | OCH$_3$ | O | CH | |
| 190 | —CH$_2$—C(CH$_3$)=CH$_2$ | 3-NO$_2$ | OCH$_3$ | OCH$_3$ | O | N | |
| 191 | —CH$_2$—C(CH$_3$)=CH$_2$ | 3-NO$_2$ | OCH$_3$ | OCH$_3$ | O | CH | |
| 192 | —CH$_2$—CH=C(Cl)—CH$_3$ | 3-NO$_2$ | OCH$_3$ | OCH$_3$ | O | CH | |
| 193 | —CH$_2$—CH=C(Cl)—CH$_3$ | 3-NO$_2$ | OCH$_3$ | CH$_3$ | O | CH | |
| 194 | —CH$_2$—CH=C(Cl)—CH$_3$ | 3-NO$_2$ | OCH$_3$ | CH$_3$ | O | N | |
| 195 | —CH$_2$—CH=CH$_2$ | 3-CH$_3$ | OCH$_3$ | CH$_3$ | O | N | m.p. 255–256° |
| 196 | —CH$_2$—CH=CH$_2$ | 3-CH$_3$ | OCH$_3$ | CH$_3$ | O | CH | m.p. 163–164° |
| 197 | —CH$_2$—CH=CH$_2$ | 3-CH$_3$ | C$_2$H$_5$ | CH$_3$ | O | N | |
| 198 | —CH$_2$—CH=CH$_2$ | 3-CH$_3$ | OCH$_3$ | CH$_3$ | O | N | m.p. 183–184° |
| 199 | —CH$_2$—CH=CH$_2$ | 3-CH$_3$ | OCH$_3$ | CH$_3$ | O | CH | |
| 200 | —CH$_2$—CH=CH$_2$ | 3-Cl | OCH$_3$ | CH$_3$ | O | CH | |
| 201 | —CH$_2$—CH=CH$_2$ | 3-Cl | OCH$_3$ | CH$_3$ | O | N | |
| 202 | —CH$_2$—CH=CH$_2$ | 3-Cl | OCH$_3$ | OCH$_3$ | O | N | |
| 203 | —CH$_2$—CH=CH$_2$ | 3-Cl | OCH$_3$ | OCH$_3$ | O | CH | |
| 204 | —CH$_2$—C(CH$_3$)=CH$_2$ | 3-Cl | OCH$_3$ | OCH$_3$ | O | N | |
| 205 | —CH$_2$—C(CH$_3$)=CH$_2$ | 3-Cl | OCH$_3$ | CH$_3$ | O | N | |

TABLE 3-continued

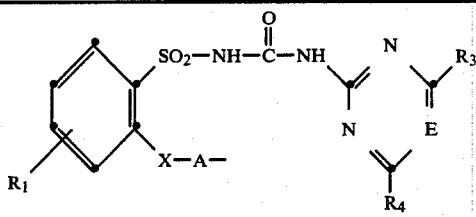

| No. | A | $R_1$ | $R_3$ | $R_4$ | X | E | Physical data (°C.) |
|---|---|---|---|---|---|---|---|
| 206 | $-CH_2-\underset{\underset{CH_3}{\mid}}{C}=CH_2$ | 3-Cl | $OCH_3$ | $CH_3$ | O | CH | |
| 207 | $-CH_2-CH=CH-CH_3$ | 3-Cl | $CH_3$ | $OCH_3$ | O | N | |
| 208 | $-CH_2-CH=CH-CH_3$ | 3-Cl | $CH_3$ | $OCH_3$ | O | CH | |
| 209 | $-CH_2-\underset{\underset{CH_3}{\mid}}{C}=CH_2$ | 3-$OCH_3$ | $CH_3$ | $OCH_3$ | O | CH | |
| 210 | $-CH_2-\underset{\underset{CH_3}{\mid}}{C}=CH_2$ | 3-$OCH_3$ | $CH_3$ | $OCH_3$ | O | N | |
| 211 | $-CH_2-CH=CH_2$ | 3-$OCH_3$ | $CH_3$ | $OCH_3$ | O | N | |
| 212 | $-CH_2-CH=CH_2$ | 3-$OCH_3$ | $CH_3$ | $OCH_3$ | O | CH | |
| 213 | $-CH_2-CH=CH_2$ | 3-$OCH_3$ | $OCH_3$ | $OCH_3$ | O | CH | |
| 214 | $-CH_2-CH=CH_2$ | 3-$OCH_3$ | $C_2H_5$ | $OCH_3$ | O | N | |
| 215 | $-CH_2-CH=CH_2$ | 3-$OCH_3$ | $OCH_3$ | $OCH_3$ | O | N | |

TABLE 4

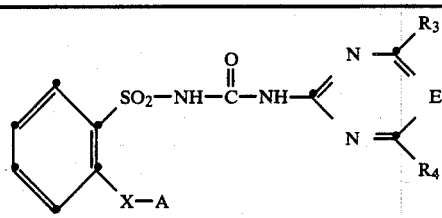

| No. | A | $R_3$ | $R_4$ | X | E | Physical data (°C.) |
|---|---|---|---|---|---|---|
| 301 | $-CH_2-\underset{\underset{CH_3}{\mid}}{C}=CH_2$ | $CH_3$ | $CH_3$ | O | N | m.p. 95–103° |
| 302 | $-CH_2-\underset{\underset{CH_3}{\mid}}{C}=CH_2$ | $CH_3$ | $OCH_3$ | O | N | m.p. 142–143° |
| 303 | $-CH_2-\underset{\underset{CH_3}{\mid}}{C}=CH_2$ | $OCH_3$ | $OCH_3$ | O | N | m.p. 145–153° |
| 304 | $-CH_2-\underset{\underset{CH_3}{\mid}}{C}=CH_2$ | $OCH_3$ | $OC_2H_5$ | O | N | |
| 305 | $-CH_2-\underset{\underset{CH_3}{\mid}}{C}=CH_2$ | $-CH_2-CH_3$ | $OCH_3$ | O | N | m.p. 150–152° |
| 306 | $-CH_2-\underset{\underset{CH_3}{\mid}}{C}=CH_2$ | $-CH_2-CH_3$ | $CH_3$ | O | N | m.p. 129–130° |
| 307 | $-CH_2-\underset{\underset{CH_3}{\mid}}{C}=CH_2$ | Cl | $OCH_3$ | O | N | |
| 308 | $-CH_2-\underset{\underset{CH_3}{\mid}}{C}=CH_2$ | $-OCH(CH_3)_2$ | $OCH_3$ | O | N | |

TABLE 4-continued

[Structure: benzene ring with SO2—NH—C(=O)—NH—C(=N–CR3)(E)(=N–CR4) triazine/pyrimidine system, and X—A substituent on benzene]

| No. | A | R₃ | R₄ | X | E | Physical data (°C.) |
|---|---|---|---|---|---|---|
| 309 | —CH₂—C(CH₃)=CH₂ | —OCH(CH₃)₂ | OCH₃ | O | N | |
| 310 | —CH₂—C(CH₃)=CH₂ | —OCH(CH₃)₂ | CH₃ | O | N | |
| 311 | —CH₂—C(CH₃)=CH₂ | OCH₃ | SCH₃ | O | N | |
| 312 | —CH₂—C(CH₃)=CH₂ | OC₂H₅ | OC₂H₅ | O | N | m.p. 118–120° |
| 313 | —CH₂—C(CH₃)=CH₂ | OCH₃ | —CH₂OCH₃ | O | N | |
| 314 | —CH₂—C(CH₃)=CH₂ | CH₂Cl | OCH₃ | O | N | |
| 315 | —CH₂—C(CH₃)=CH₂ | CH₂F | OCH₃ | O | N | |
| 316 | —CH₂—C(CH₃)=CH₂ | CH₃ | OCH₃ | O | CH | m.p. 172–177° |
| 317 | —CH₂—C(CH₃)=CH₂ | OCH₃ | OCH₃ | O | CH | |
| 318 | —CH₂—C(CH₃)=CH₂ | CH₃ | CH₃ | O | CH | |
| 319 | —CH₂—C(CH₃)=CH₂ | C₂H₅ | OCH₃ | O | CH | |
| 320 | —CH₂—C(CH₃)=CH₂ | OCH₃ | Cl | O | CH | m.p. 179–180° |
| 321 | —CH₂—C(CH₃)=CH₂ | CH₃ | Cl | O | CH | |
| 322 | —CH₂—C(CH₃)=CH₂ | CF₃ | OCH₃ | O | CH | |
| 323 | —CH₂—C(CH₃)=CH₂ | —CH₂—OCH₃ | OCH₃ | O | CH | |
| 324 | —CH₂—C(CH₃)=CH₂ | Br | OCH₃ | O | CH | |
| 325 | —CH₂—C(CH₃)=CH₂ | Br | CH₃ | O | CH | |

TABLE 4-continued

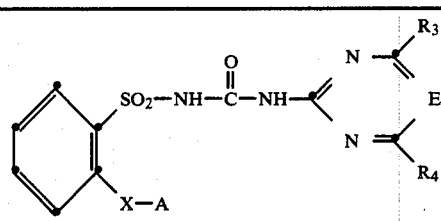

| No. | A | R₃ | R₄ | X | E | Physical data (°C.) |
|---|---|---|---|---|---|---|
| 326 | −CH₂−C(CH₃)=CH₂ | OCH₃ | SCH₃ | O | CH | |
| 327 | −CH₂−C(CH₃)=CH₂ | CH₃ | SCH₃ | O | CH | |
| 328 | −CH₂−C(CH₃)=CH₂ | OCH₃ | OC₂H₅ | O | CH | |
| 329 | −CH₂−CH=CH−CH₃ | CH₃ | OCH₃ | O | N | m.p. 163–164° |
| 330 | −CH₂−CH=CH−CH₃ | CH₃ | CH₃ | O | N | |
| 331 | −CH₂−CH=CH−CH₃ | C₂H₅ | OCH₃ | O | N | m.p. 139–140° |
| 332 | −CH₂−CH=CH−CH₃ | C₂H₅ | CH₃ | O | N | m.p. 148–151° |
| 333 | −CH₂−CH=CH−CH₃ | OCH₃ | OCH₃ | O | N | m.p. 148–149° |
| 334 | −CH₂−CH=CH−CH₃ | OCH₃ | OC₂H₅ | O | N | |
| 335 | −CH₂−CH=CH−CH₃ | OC₂H₅ | OC₂H₅ | O | N | |
| 336 | −CH₂−CH=CH−CH₃ | −CH₂−OCH₃ | OCH₃ | O | N | |
| 337 | −CH₂−CH=CH−CH₃ | CH₃ | OCH₃ | O | CH | m.p. 185–186° |
| 338 | −CH₂−CH=CH−CH₃ | OCH₃ | OCH₃ | O | CH | |
| 339 | −CH₂−CH=CH−CH₃ | CH₃ | CH₃ | O | CH | |
| 340 | −CH₂−CH=CH−CH₃ | −CH₂−OCH₃ | OCH₃ | O | CH | |
| 341 | −CH₂−CH=CH−CH₃ | CH₃ | Cl | O | CH | |
| 342 | −CH₂−CH=CH−CH₃ | OCH₃ | Cl | O | CH | |
| 343 | −CH₂−CH=CH−CG₃ | OCH₃ | OC₂H₅ | O | CH | |
| 344 | −CH₂−CH=C(CH₃)CH₃ | CH₃ | OCH₃ | O | N | |
| 345 | −CH₂−CH=C(CH₃)CH₃ | CH₃ | CH₃ | O | N | |
| 346 | −CH₂−CH=C(CH₃)CH₃ | C₂H₅ | CH₃ | O | N | |
| 347 | −CH₂−CH=C(CH₃)CH₃ | C₂H₅ | OCH₃ | O | N | |
| 348 | −CH₂−CH=C(CH₃)CH₃ | OCH₃ | OCH₃ | O | N | |
| 349 | −CH₂−CH=C(CH₃)CH₃ | OCH₃ | OC₂H₅ | O | N | |
| 350 | −CH₂−CH=C(CH₃)CH₃ | OC₂H₅ | OC₂H₅ | O | N | |

TABLE 4-continued

[Structure: benzene ring with SO₂—NH—C(=O)—NH—C(=N-R₃)(E)(N=R₄ via E linkage), and X—A substituent on ring]

| No. | A | R₃ | R₄ | X | E | Physical data (°C.) |
|-----|---|-----|-----|---|---|---------------------|
| 351 | —CH₂—CH=C(CH₃)CH₃ | —CH₂—OCH₃ | OCH₃ | O | N | |
| 352 | —CH₂—CH=C(CH₃)CH₃ | CH₃ | OCH₃ | O | CH | |
| 353 | —CH₂—CH=C(CH₃)CH₃ | OCH₃ | OCH₃ | O | CH | |
| 354 | —CH₂—CH=C(CH₃)CH₃ | CH₃ | CH₃ | O | CH | |
| 355 | —CH₂—CH=C(CH₃)CH₃ | OCH₃ | Cl | O | CH | |
| 356 | —CH₂—CH=C(CH₃)CH₃ | CH₃ | Cl | O | CH | |
| 357 | —CH₂—CH=C(CH₃)CH₃ | OCH₃ | OC₂H₅ | O | CH | |
| 358 | —CH₂—C(Cl)=CH₂ | CH₃ | OCH₃ | O | N | |
| 359 | —CH₂—C(Cl)=CH₂ | CH₃ | CH₃ | O | N | |
| 360 | —CH₂—C(Cl)=CH₂ | C₂H₅ | CH₃ | O | N | |
| 361 | —CH₂—C(Cl)=CH₂ | C₂H₅ | OCH₃ | O | N | |
| 362 | —CH₂—C(Cl)=CH₂ | OCH₃ | OCH₃ | O | N | |
| 363 | —CH₂—C(Cl)=CH₂ | OCH₃ | OC₂H₅ | O | N | |
| 364 | —CH₂—C(Cl)=CH₂ | OC₂H₅ | OC₂H₅ | O | N | |

TABLE 4-continued

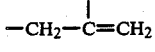

| No. | A | R₃ | R₄ | X | E | Physical data (°C.) |
|---|---|---|---|---|---|---|
| 365 | -CH₂-C(Cl)=CH₂ | -CH₂-OCH₃ | OCH₃ | O | N | |
| 366 | -CH₂-C(Cl)=CH₂ | CH₃ | OCH₃ | O | CH | |
| 367 | -CH₂-C(Cl)=CH₂ | OCH₃ | OCH₃ | O | CH | |
| 368 | -CH₂-C(Cl)=CH₂ | CH₃ | CH₃ | O | CH | |
| 369 | -CH₂-C(Cl)=CH₂ | OCH₃ | Cl | O | CH | |
| 370 | -CH₂-C(Cl)=CH₂ | CH₃ | Cl | O | CH | |
| 371 | -CH₂-C(Cl)=CH₂ | OC₂H₅ | OCH₃ | O | CH | |
| 372 | -CH₂-C(Cl)=CH₂ | -CH₂-OCH₃ | OCH₃ | O | CH | |
| 373 | -CH₂-OCH₃ | CH₃ | OCH₃ | O | N | m.p. 155-157° |
| 374 | -CH₂-OCH₃ | OCH₃ | OCH₃ | O | N | |
| 375 | -CH₂-OCH₃ | C₂H₅ | OCH₃ | O | N | |
| 376 | -CH₂-OCH₃ | C₂H₅ | CH₃ | O | N | |
| 377 | -CH₂-OCH₃ | OCH₃ | OCH₃ | O | N | |
| 378 | -CH₂-OCH₃ | OCH₃ | OC₂H₅ | O | N | |
| 379 | -CH₂-OCH₃ | OC₂H₅ | OC₂H₅ | O | N | |
| 380 | -CH₂-OCH₃ | -CH₂-OCH₃ | OCH₃ | O | N | |
| 381 | -CH₂-OCH₃ | OCH₃ | SCH₃ | O | N | |
| 382 | -CH₂-OCH₃ | OCH₃ | CH₃ | O | CH | m.p. 168-175° |
| 383 | -CH₂-OCH₃ | OCH₃ | OCH₃ | O | CH | |
| 384 | -CH₂-OCH₃ | CH₃ | CH₃ | O | CH | |
| 385 | -CH₂-OCH₃ | CH₃ | Cl | O | CH | m.p. 137-143° |
| 386 | -CH₂-OCH₃ | OCH₃ | Cl | O | CH | |
| 387 | -CH₂-OCH₃ | C₂H₅ | OCH₃ | O | CH | |
| 388 | -CH₂-OCH₃ | OC₂H₅ | OCH₃ | O | CH | |
| 389 | -CH₂-C(Cl)=CH₂ | C₂H₅ | OCH₃ | O | CH | |
| 390 | -CH₂-CH=C(CH₃)CH₃ | C₂H₅ | OCH₃ | O | CH | |
| 391 | -CH₂-CH=CH-CH₃ | C₂H₅ | OCH₃ | O | CH | |
| 392 | -CH₂-S-CH₃ | CH₃ | OCH₃ | O | N | |
| 393 | -CH₂-S-CH₃ | CH₃ | CH₃ | O | N | |
| 394 | -CH₂-S-CH₃ | C₂H₅ | CH₃ | O | N | |
| 395 | -CH₂-S-CH₃ | C₂H₅ | OCH₃ | O | N | |
| 396 | -CH₂-S-CH₃ | OCH₃ | OCH₃ | O | N | |
| 397 | -CH₂-S-CH₃ | OCH₃ | OC₂H₅ | O | N | |
| 398 | -CH₂-S-CH₃ | -CH₂-OCH₃ | OCH₃ | O | N | |
| 399 | -CH₂-S-CH₃ | CH₃ | OCH₃ | O | CH | |
| 400 | -CH₂-S-CH₃ | OCH₃ | OCH₃ | O | CH | |
| 401 | -CH₂-S-CH₃ | CH₃ | CH₃ | O | CH | |

TABLE 4-continued

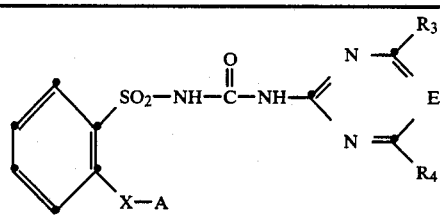

| No. | A | R₃ | R₄ | X | E | Physical data (°C.) |
|---|---|---|---|---|---|---|
| 402 | —CH₂—S—CH₃ | C₂H₅ | OCH₃ | O | CH | |
| 403 | —CH₂—S—CH₃ | OCH₃ | Cl | O | CH | |
| 404 | —CH₂—S—CH₃ | CH₃ | Cl | O | CH | |
| 405 | —CH₂—S—CH₃ | OCH₃ | OC₂H₅ | O | CH | |
| 406 | —CH₂—CH₂—OC₂H₅ | CH₃ | OCH₃ | O | N | |
| 407 | —CH₂—CH₂—OC₂H₅ | CH₃ | CH₃ | O | N | |
| 408 | —CH₂—CH₂—OC₂H₅ | C₂H₅ | CH₃ | O | N | |
| 409 | —CH₂—CH₂—OC₂H₅ | C₂H₅ | OCH₃ | O | N | |
| 410 | —CH₂—CH₂—OC₂H₅ | OCH₃ | OCH₃ | O | N | |
| 411 | —CH₂—CH₂—OC₂H₅ | CH₃ | OCH₃ | O | CH | |
| 412 | —CH₂—CH₂—OC₂H₅ | OCH₃ | OCH₃ | O | CH | |
| 413 | —CH₂—CH₂—OC₂H₅ | OCH₃ | Cl | O | CH | m.p. 166–168° |
| 414 | —CH₂—CH₂—OC₂H₅ | CH₃ | Cl | O | CH | |
| 415 | —CH₂—CH=CH₂ | CH₃ | C₂H₅ | S | N | |
| 416 | —CH₂—CH=CH₂ | OCH₃ | C₂H₅ | S | N | |
| 417 | —CH₂—CH=CH₂ | CH₃ | OCH₃ | S | CH | |
| 418 | —CH₂—CH=CH₂ | OCH₃ | OCH₃ | S | CH | |
| 419 | —CH₂—CH=CH₂ | CH₃ | OCH₃ | SO | N | |
| 420 | —CH₂—CH=CH₂ | OCH₃ | OCH₃ | SO | N | |
| 421 | —CH₂—CH=CH₂ | OCH₃ | OC₂H₅ | SO | N | |
| 422 | —CH₂—CH=CH₂ | OCH₃ | OCH₃ | SO | CH | |
| 423 | —CH₂—CH=CH₂ | CH₃ | OCH₃ | SO | CH | |
| 424 | —CH₂—CH=CH₂ | CH₃ | OCH₃ | SO₂ | N | |
| 425 | —CH₂—CH=CH₂ | OCH₃ | OCH₃ | SO₂ | N | |
| 426 | —CH₂—CH=CH₂ | OCH₃ | OCH₃ | SO₂ | CH | |
| 427 | —CH₂—CH=CH₂ | CH₃ | OCH₃ | SO₂ | CH | |
| 428 | —CH₂—CH=CH—CH₃ | CH₃ | OCH₃ | SO₂ | N | |
| 429 | —CH₂—CH=CH—CH₃ | CH₃ | OCH₃ | SO₂ | CH | |
| 430 | —CH₂—CH=CH—CH₃ | CH₃ | OCH₃ | SO | CH | |
| 431 | —CH₂—CH=CH—CH₃ | CH₃ | OCH₃ | SO | N | |
| 432 | —CH₂—SO—CH₃ | CH₃ | OCH₃ | O | N | |
| 433 | —CH₂—SO—CH₃ | CH₃ | OCH₃ | O | CH | |
| 434 | —CH₂—SO—CH₃ | OCH₃ | OCH₃ | O | N | |
| 435 | —CH₂—SO—CH₃ | OCH₃ | OCH₃ | O | CH | |
| 436 | —CH₂—SO₂—CH₃ | OCH₃ | OCH₃ | O | CH | |
| 437 | —CH₂—SO₂—CH₃ | CH₃ | OCH₃ | O | CH | |
| 438 | —CH₂—SO₂—CH₃ | CH₃ | CH₃ | O | CH | |
| 439 | —CH₂—SO₂—CH₃ | CH₃ | OCH₃ | O | N | |
| 440 | —CH₂—SO₂—CH₃ | OCH₃ | OCH₃ | O | N | |
| 441 | —CH₂—CH₂—SO—CH₃ | OCH₃ | OCH₃ | O | N | |
| 442 | —CH₂—CH₂—SO—CH₃ | OCH₃ | CH₃ | O | N | |
| 443 | —CH₂—CH₂—SO—CH₃ | OCH₃ | CH₃ | O | CH | |
| 444 | —CH₂—CH₂—SO₂—CH₃ | OCH₃ | CH₃ | O | CH | |
| 445 | —CH₂—CH₂—SO₂—CH₃ | OCH₃ | CH₃ | O | N | |
| 446 | —CH₂—CH₂—SO₂—CH₃ | CH₃ | OCH₃ | O | N | |
| 447 | —CH₂—C(CH₃)=CH₂ | CH₃ | OCH₃ | S | N | |
| 448 | —CH₂—C(CH₃)=CH₂ | CH₃ | OCH₃ | S | CH | |
| 449 | —CH₂—CH=C(CH₃)CH₃ | CH₃ | OCH₃ | S | CH | |
| 450 | —CH₂—CH=C(CH₃)CH₃ | CH₃ | OCH₃ | S | N | |
| 451 | —CH₂—CH=CH₃ | CH₃ | OCH₃ | S | N | |
| 452 | —CH₂—CH=CH₃ | CH₃ | OCH₃ | S | CH | |
| 453 | —CH₂—CH₂—OCH₃ | CH₃ | OCH₃ | S | CH | |
| 454 | —CH₂—CH₂—OCH₃ | CH₃ | OCH₃ | S | N | |

TABLE 4-continued $$\text{Structure: benzene ring with SO}_2\text{-NH-C(=O)-NH-C(=N-)(N=) pyrimidine/triazine with } R_3, R_4, E; \text{ ortho substituent X-A}$$

| No. | A | $R_3$ | $R_4$ | X | E | Physical data (°C.) |
|---|---|---|---|---|---|---|
| 455 | —(CH$_2$)$_2$—CH=CH$_2$ | CH$_3$ | OCH$_3$ | O | N | |
| 456 | —(CH$_2$)$_2$—CH=CH$_2$ | CH$_3$ | OCH$_3$ | O | CH | |
| 457 | —(CH$_2$)$_2$—CH=CH$_2$ | CH$_3$ | CH$_3$ | O | N | |
| 458 | —(CH$_2$)$_2$—CH=CH$_2$ | CH$_3$ | CH$_3$ | O | CH | |
| 459 | —(CH$_2$)$_3$—CH=CH$_2$ | CH$_3$ | OCH$_3$ | O | N | |
| 460 | —(CH$_2$)$_3$—CH=CH$_2$ | CH$_3$ | OCH$_3$ | O | CH | |
| 461 | —CH(CH$_3$)—CH=CH$_2$ | CH$_3$ | OCH$_3$ | O | N | |
| 462 | —CH(CH$_3$)—CH=CH$_2$ | CH$_3$ | OCH$_3$ | O | CH | |
| 463 | —CH$_2$—OC$_2$H$_5$ | CH$_3$ | OCH$_3$ | O | CH | |
| 464 | —CH$_2$—OC$_2$H$_5$ | CH$_3$ | OCH$_3$ | O | N | |
| 465 | —CH$_2$—OC$_2$H$_5$ | C$_2$H$_5$ | OCH$_3$ | O | N | |
| 466 | —CH$_2$—OC$_2$H$_5$ | CH$_3$ | CH$_3$ | O | N | |
| 467 | —CH$_2$—OC$_2$H$_5$ | CH$_3$ | CH$_3$ | O | CH | |
| 468 | —CH$_2$—CH$_2$—OCH$_3$ | CH$_3$ | CH$_3$ | O | CH | |
| 469 | —CH$_2$—CH$_2$—OCH$_3$ | CH$_3$ | CH$_3$ | O | N | |
| 470 | —CH$_2$—CH$_2$—OCH$_3$ | CH$_3$ | OCH$_3$ | O | N | m.p. 134–138° |
| 471 | —CH$_2$—CH$_2$—OCH$_3$ | CH$_3$ | OCH$_3$ | O | CH | m.p. 160–162° |
| 472 | —CH$_2$—CH$_2$—SCH$_3$ | CH$_3$ | OCH$_3$ | O | CH | |
| 473 | —CH$_2$—CH$_2$—SCH$_3$ | CH$_3$ | OCH$_3$ | O | N | |
| 474 | —CH$_2$—C(Cl)=CH—Cl | CH$_3$ | OCH$_3$ | O | N | |
| 475 | —CH$_2$—C(Cl)=CH—Cl | CH$_3$ | OCH$_3$ | O | CH | |
| 476 | —CH$_2$—CH=C(Cl)—CH$_3$ | CH$_3$ | OCH$_3$ | O | CH | |
| 477 | —CH$_2$—CH=C(Cl)—CH$_3$ | CH$_3$ | OCH$_3$ | O | N | |
| 479 | —CH$_2$—CH=CCl$_2$ | CH$_3$ | OCH$_3$ | O | N | |
| 479 | —CH$_2$—CH=CCl$_2$ | CH$_3$ | OCH$_3$ | O | CH | |
| 480 | —CH$_2$—CH$_2$—O—CH$_2$—CH=CH$_2$ | CH$_3$ | OCH$_3$ | O | CH | |
| 481 | —CH$_2$—CH$_2$—O—CH$_2$—CH=CH$_2$ | CH$_3$ | OCH$_3$ | O | N | |
| 482 | —CCl=CCl$_2$ | CH$_3$ | OCH$_3$ | O | N | |
| 483 | —CCl=CHCl | OCH$_3$ | OCH$_3$ | O | CH | |
| 484 | —CCl=CCl$_2$ | OCH$_3$ | OCH$_3$ | O | N | |
| 485 | —CCl=CCl$_2$ | CH$_3$ | OCH$_3$ | O | CH | |
| 486 | —CCl=CCl$_2$ | OCH$_3$ | OCH$_3$ | O | CH | |
| 487 | —CCl=CCl$_2$ | CH$_3$ | Cl | O | CH | |
| 488 | —CCl=CCl$_2$ | OCH$_3$ | Cl | O | N | |
| 489 | —CF=CF$_2$ | OCH$_3$ | Cl | O | N | |
| 490 | —CF=CF$_2$ | CH$_3$ | Cl | O | CH | |
| 491 | —CH=CCl$_2$ | OCH$_3$ | OCH$_3$ | O | N | |

TABLE 4-continued

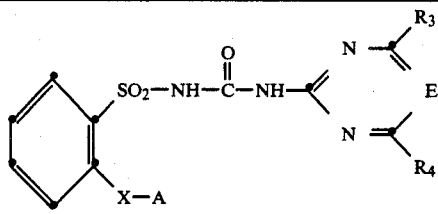

| No. | A | $R_3$ | $R_4$ | X | E | Physical data (°C.) |
|---|---|---|---|---|---|---|
| 492 | —CH=CCl$_2$ | CH$_3$ | OCH$_3$ | O | CH | |
| 493 | —CH=CCl$_2$ | OCH$_3$ | OCH$_3$ | O | CH | |
| 494 | —CH=CCl$_2$ | C$_2$H$_5$ | OCH$_3$ | O | N | |
| 495 | —CF=CF$_2$ | C$_2$H$_5$ | OCH$_2$ | O | N | |
| 496 | —CCl=CHCl | OCH$_3$ | OCH$_3$ | S | N | |
| 497 | —CCl=CHCl | CH$_3$ | OCH$_3$ | O | N | m.p. 169–172° |
| 498 | —CCl=CHCl | C$_2$H$_5$ | OCH$_3$ | O | N | |
| 499 | —CCl=CHCl | CH$_3$ | CH$_3$ | O | N | |
| 500 | —CCl=CHCl | OCH$_3$ | Cl | O | CH | m.p. 196–198° |
| 501 | —CCl=CHCl | OCH$_3$ | OC$_2$H$_5$ | O | N | |
| 502 | —CCl=CHCl | OCH$_3$ | OCH$_3$ | O | CH | |
| 503 | —CCl=CHCl | C$_2$H$_5$ | OCH$_3$ | O | CH | |
| 504 | —CCl=CHCl | CH$_3$ | Cl | O | CH | |
| 505 | —CCl=CHCl | CH$_3$ | OCH$_3$ | S | CH | |
| 506 | —CCl=CHCl | OCH$_3$ | OCH$_3$ | S | CH | |
| 507 | —CF=CF$_2$ | CH$_3$ | OCH$_3$ | O | N | |
| 508 | —CF=CF$_2$ | OCH$_3$ | OCH$_3$ | O | N | |
| 509 | —CF=CF$_2$ | CH$_3$ | OCH$_3$ | O | CH | |
| 510 | —CF=CF$_2$ | OCH$_3$ | OCH$_3$ | O | CH | |
| 511 | —CH$_2$—CH=CH$_2$ | —CH(CH$_3$)$_2$ | OCH$_3$ | O | CH | |
| 512 | —CH$_2$—CH=CH$_2$ | OCH$_3$ | SC$_2$H$_5$ | O | CH | |
| 513 | —CH$_2$—CH=CH$_2$ | OCH$_3$ | SC$_2$H$_5$ | O | N | |
| 514 | —CH$_2$—CH=CH$_2$ | OCH$_3$ | —SCH(CH$_3$)$_2$ | O | N | |
| 515 | —CH$_2$—CH=CH$_2$ | Cl | CH$_3$ | O | N | m.p. 128–130° |
| 516 | —CH$_2$—CH=CH$_2$ | CH$_3$ | Br | O | N | |
| 517 | —CH$_2$—CH=CH$_2$ | CHF$_2$ | OCH$_3$ | O | N | |
| 518 | —CH$_2$—CH=CH$_2$ | CHF$_2$ | CH$_3$ | O | N | |
| 519 | —CH$_2$—CH=CH$_2$ | —CH$_2$CF$_3$ | Cl | O | N | |
| 520 | —CH$_2$—CH=CH$_2$ | —CH$_2$CF$_3$ | OCH$_3$ | O | N | |
| 521 | —CH$_2$—CH=CH$_2$ | —CH$_2$CF$_3$ | CH$_3$ | O | N | |
| 522 | —CH$_2$—CH=CH$_2$ | OC$_2$H$_5$ | OC$_2$H$_5$ | O | N | m.p. 138–142° |
| 523 | —CH$_2$—CH=CH$_2$ | OC$_2$H$_5$ | OC$_2$H$_5$ | O | CH | |
| 524 | —CH$_2$—CH=CH$_2$ | C$_2$H$_5$ | OCH$_3$ | O | N | m.p. 206° |
| 525 | —CH$_2$—CH=CH$_2$ | C$_2$H$_5$ | OC$_2$H$_5$ | O | N | |
| 526 | —CH$_2$—CH=CH$_2$ | CH$_3$ | OC$_2$H$_5$ | O | N | m.p. 129–131° |
| 527 | —CH$_2$—CH=CH$_2$ | CH$_3$ | CH$_3$ | O | CH | m.p. 180–182° |
| 528 | —CH$_2$—CH=CH$_2$ | CH$_3$ | OCH$_3$ | O | CH | m.p. 98–100° |
| 529 | —CH$_2$—CH=CH$_2$ | CH$_3$ | Br | O | N | |
| 530 | —CH$_2$—CH=CH$_2$ | CH$_3$ | H | O | N | |
| 531 | —CH$_2$—CH=CH$_2$ | C$_2$H$_5$ | Cl | O | CH | |
| 532 | —CH$_2$—CH=CH$_2$ | CH$_3$ | Cl | O | CH | m.p. 153–154° |
| 533 | —CH$_2$—CH=CH$_2$ | CH$_3$ | SCH$_3$ | O | CH | |
| 534 | —CH$_2$—CH=CH$_2$ | CH$_3$ | F | O | CH | |
| 535 | —CH$_2$—CH=CH$_2$ | CH$_3$ | Br | O | CH | |
| 536 | —CH$_2$—CH=CH$_2$ | C$_2$H$_5$ | OC$_2$H$_5$ | O | CH | |
| 537 | —CH$_2$—CH=CH$_2$ | C$_2$H$_5$ | SCH$_3$ | O | CH | |
| 538 | —CH$_2$—CH=CH$_2$ | CF$_3$ | CH$_3$ | O | CH | |
| 539 | —CH$_2$—CH=CH$_2$ | CH$_2$Cl | CH$_3$ | O | CH | |
| 540 | —CH$_2$—CH=CH$_2$ | CH$_2$Cl | OCH$_3$ | O | CH | |
| 541 | —CH$_2$—CH=CH$_2$ | OCH$_3$ | Cl | O | CH | m.p. 173–179° |
| 542 | —CH$_2$—CH=CH$_2$ | Cl | Cl | O | CH | |
| 543 | —CH$_2$—CH=CH$_2$ | OCH$_3$ | SCH$_3$ | O | CH | |
| 544 | —CH$_2$—CH=CH$_2$ | OCH$_3$ | —OCH(CH$_3$)$_2$ | O | CH | |
| 545 | —CH$_2$—CH=CH$_2$ | CH$_2$F | OCH$_3$ | O | CH | |
| 546 | —CH$_2$—CH=CH$_2$ | CH$_2$F | CH$_3$ | O | CH | |
| 547 | —CH$_2$—CH=CH$_2$ | CF$_3$ | OCH$_3$ | O | CH | |
| 548 | —CH$_2$—CH=CH$_2$ | C$_2$H$_5$ | —OCH(CH$_3$)$_2$ | O | N | |
| 549 | —CH$_2$—CH=CH$_2$ | C$_2$H$_5$ | Cl | O | N | |
| 550 | —CH$_2$—CH=CH$_2$ | C$_2$H$_5$ | SCH$_3$ | O | N | |
| 551 | —CH$_2$—CH=CH$_2$ | C$_2$H$_5$ | CH$_3$ | O | N | m.p. 128–131° |
| 552 | —CH$_2$—CH=CH$_2$ | C$_2$H$_5$ | C$_2$H$_5$ | O | N | |
| 553 | —CH$_2$—CH=CH$_2$ | OCH$_3$ | —OCH(CH$_3$)$_2$ | O | N | m.p. 119–120° |
| 554 | —CH$_2$—CH=CH$_2$ | OCH$_3$ | —OCH(CH$_3$)—CH$_2$CH$_3$ | O | N | |
| 555 | —CH$_2$—CH=CH$_2$ | CH$_3$ | —CH(CH$_3$)$_2$ | O | N | m.p. 96–98° |
| 556 | —CH$_2$—CH=CH$_2$ | —CH(CH$_3$)$_2$ | Cl | O | N | |
| 557 | —CH$_2$—CH=CH$_2$ | —CH(CH$_3$)$_2$ | OCH$_3$ | O | N | m.p. 124–128° |
| 558 | —CH$_2$—CH=CH$_2$ | —CH(CH$_3$)$_2$ | OC$_2$H$_5$ | O | N | |
| 559 | —CH$_2$—CH=CH$_2$ | —CH(CH$_3$)$_2$ | SCH$_3$ | O | N | |
| 560 | —CH$_2$—CH=CH$_2$ | CH$_2$Cl | CH$_3$ | O | N | |

TABLE 4-continued

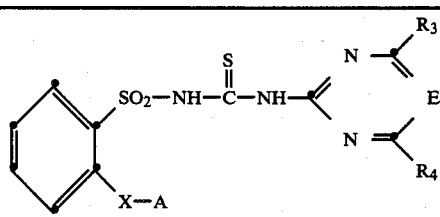

| No. | A | R₃ | R₄ | X | E | Physical data (°C.) |
|---|---|---|---|---|---|---|
| 561 | —CH₂—CH=CH₂ | CH₂Cl | OCH₃ | O | N | |
| 562 | —CH₂—CH=CH₂ | CH₂F | CH₃ | O | N | |
| 563 | —CH₂—CH=CH₂ | CH₂F | OCH₃ | O | N | |
| 564 | —CH₂—CH=CH₂ | CH₂F | OC₂H₅ | O | N | |
| 565 | —CH₂—CH=CH₂ | —CH₂—OCH₃ | C₂H₅ | O | N | |
| 566 | —CH₂—CH=CH₂ | —CH₂—SCH₃ | OCH₃ | O | N | |
| 567 | —CH₂—CH=CH₂ | —CH₂—SCH₃ | CH₃ | O | N | |
| 568 | —CH₂—CH=CH₂ | —CH₂—SCH₃ | SCH₃ | O | N | |
| 569 | —CH₂—CH=CH₂ | —CH₂—SCH₃ | Cl | O | N | |
| 570 | —CH₂—CH=CH₂ | —CH₂—SCH₃ | OC₂H₅ | O | N | |
| 571 | —CH₂—CH=CH₂ | SCH₃ | Cl | O | N | |
| 572 | —CH₂—CH=CH₂ | SCH₃ | OCH₃ | O | N | |
| 573 | —CH₂—CH=CH₂ | SCH₃ | OC₂H₅ | O | N | |
| 574 | —CH₂—CH=CH₂ | SCH₃ | —OCH(CH₃)₂ | O | N | |
| 575 | —CH₂—CH=CH₂ | —OCH(CH₃)₂ | Cl | O | N | |
| 576 | —CH₂—CH=CH₂ | CF₃ | OCH₃ | O | N | |
| 577 | —CH₂—CH=CH₂ | CF₃ | CH₃ | O | N | |
| 578 | —CH₂—CH=CH₂ | CF₃ | OC₂H₅ | O | N | |
| 579 | —CH₂—CH=CH₂ | CCl₃ | OCH₃ | O | N | |
| 580 | —CH₂—CH=CH₂ | CCl₃ | SCH₃ | O | N | |
| 581 | —CH₂—CH=CH₂ | CH₃ | Cl | O | N | m.p. 128–130° |
| 582 | —CH₂—CH=CH₂ | OCH₃ | Cl | O | N | |
| 583 | —CH₂—CH=CH₂ | OCH₃ | F | O | N | |
| 584 | —CH₂—CH=CH₂ | OCH₃ | Br | O | N | |
| 585 | —CH₂—CH=CH₂ | CH₃ | F | O | N | |
| 586 | —CH₂—CH=CH₂ | OCH₃ | OCH₃ | O | CH | |
| 587 | —CH₂—CH=CH₂ | CH₃ | CH₃ | O | N | m.p. 139.141° |
| 588 | —CH₂—CH=CH₂ | OCH₃ | OC₂H₅ | O | N | |
| 589 | —CH₂—CH=CH₂ | OCH₃ | OC₂H₅ | O | CH | |
| 590 | —CH₂—CH=CH₂ | CH₂OCH₃ | OCH₃ | O | CH | |
| 591 | —CH₂—CH=CH₂ | CH₂OCH₃ | OCH₃ | O | N | |
| 592 | —CH₂—CH=CH₂ | C₂H₅ | OCH₃ | O | CH | |
| 593 | —CH₂—CH=CH₂ | CH₂OCH₃ | CH₃ | O | N | |
| 594 | —CH₂—CH=CH₂ | CH₃ | OCH₃ | S | N | |
| 595 | —CH₂—CH=CH₂ | OCH₃ | OCH₃ | O | N | m.p. 148–149° |
| 596 | —CH=CHCl | CH₃ | OCH₃ | O | N | |
| 597 | —CH=CHCl | CH₃ | OCH₃ | S | N | |
| 598 | —CCl=CHCl | CH₃ | OCH₃ | O | CH | |
| 599 | —CH=CCl₂ | CH₃ | OCH₃ | O | N | |
| 600 | —CCl=CHCl | OCH₃ | OCH₃ | O | N | |
| 601 | —CH₂—CH=CH₂ | CH₃ | OCH₃ | O | N | m.p. 146–147° |
| 602 | —CH₂—CH=CH₂ | OCH₃ | OCH₃ | S | N | |

TABLE 5

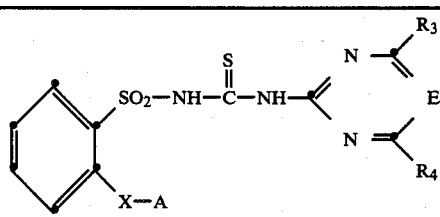

| No. | A | R₃ | R₄ | X | E |
|---|---|---|---|---|---|
| 650 | —CH₂—CH=CH₂ | CH₃ | OCH₃ | O | N |
| 651 | —CH₂—CH₂—OCH₃ | CH₃ | OCH₃ | O | N |
| 652 | —CCl=CH—Cl | CH₃ | OCH₃ | O | N |
| 653 | —CH₂—OCH₃ | CH₃ | OCH₃ | O | N |

TABLE 5-continued

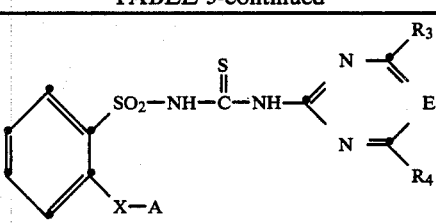

| No. | A | R₃ | R₄ | X | E |
|---|---|---|---|---|---|
| 654 | —CH₂—CH=CH—CH₃ | OCH₃ | OCH₃ | O | N |
| 655 | —CH₂—C(CH₃)=CH₂ | CH₃ | OCH₃ | O | CH |

TABLE 6

| No. | A | Position of —X—A | R₁ | R₂ | X | E | Physical data (°C.) |
|---|---|---|---|---|---|---|---|
| 701 | —CH₂—CH=CH₂ | 5 | 2-CH₃ | H | O | N | |
| 702 | —CH₂—CH=CH₂ | 5 | 2-CH₃ | H | O | CH | |
| 703 | —CH₃—C(CH₃)=CH₂ | 5 | 2-CH₃ | H | O | CH | |
| 704 | —CH₃—C(CH₃)=CH₂ | 5 | 2-CH₃ | H | O | N | |
| 705 | —CH₂—CH=CH—CH₃ | 5 | 2-CH₃ | H | O | N | |
| 706 | —CH₂—CH=CH—CH₃ | 5 | 2-CH₃ | H | O | CH | |
| 707 | —CH₂—C(Cl)=CH₂ | 5 | 2-CH₃ | H | O | CH | |
| 708 | —CH₂—C(Cl)=CH₂ | 5 | 2-CH₃ | H | O | N | |
| 709 | —CH₂—CH=CH₂ | 5 | 2-Cl | H | O | N | |
| 710 | —CH₂—CH=CH₂ | 5 | 2-Cl | H | O | CH | |
| 711 | —CH₂—C(Cl)=CH₂ | 5 | 2-Cl | H | O | CH | |
| 712 | —CH₂—C(Cl)=CH₂ | 5 | 2-Cl | H | O | N | |
| 713 | —CH₂—C(CH₃)=CH₂ | 5 | 2-Cl | H | O | N | |
| 714 | —CH₂—C(CH₃)=CH₂ | 5 | 2-Cl | H | O | CH | |
| 715 | —CH₂—O—CH₃ | 5 | 2-Cl | H | O | CH | |
| 716 | —CH₂—O—CH₃ | 5 | 2-Cl | H | O | N | |
| 717 | —CH₂—S—CH₃ | 5 | 2-Cl | H | O | N | |
| 718 | —CH₂—S—CH₃ | 5 | 2-Cl | H | O | CH | |
| 719 | —CH₂—CH=CH—CH₃ | 5 | 2-Cl | H | O | CH | |
| 720 | —CH₂—CH=CH—CH₃ | 5 | 2-Cl | H | O | N | |
| 721 | —CH₂—CH₂—OCH₃ | 5 | 2-Cl | H | O | N | |
| 722 | —CH₂—CH₂—OCH₃ | 5 | 2-Cl | H | O | CH | |
| 723 | —CH₂—OC₂H₅ | 5 | 2-Cl | H | O | N | |
| 724 | —CH₂—OC₂H₅ | 5 | 2-Cl | H | O | CH | |
| 725 | —CH₂—CH₂—SCH₃ | 5 | 2-Cl | H | O | CH | |
| 726 | —CH₂—CH₂—SCH₃ | 5 | 2-Cl | H | O | N | |
| 727 | —CH₂—CH=CH₂ | 3 | 2-CH₃ | H | O | N | |
| 728 | —CH₂—CH=CH₂ | 3 | 2-CH₃ | H | O | CH | |
| 729 | —CH₂—C(CH₃)=CH₃ | 3 | 2-CH₃ | H | O | CH | |
| 730 | —CH₂—C(CH₃)=CH₃ | 3 | 2-CH₃ | H | O | N | |
| 731 | —CH₂—CH=CH₂ | 3 | 2-OCH₃ | H | O | N | |
| 732 | —CH₂—CH=CH₂ | 3 | 2-OCH₃ | H | O | CH | |
| 733 | —CH₂—C(CH₃)=CH₂ | 3 | 2-OCH₃ | H | O | CH | |

TABLE 6-continued

| No. | A | Position of —X—A | R₁ | R₂ | X | E | Physical data (°C.) |
|---|---|---|---|---|---|---|---|
| 734 | —CH₂—C(CH₃)=CH₂ | 3 | 2-OCH₃ | H | O | N | |
| 735 | —CH₂—C(Cl)=CH₂ | 3 | 2-OCH₃ | H | O | N | |
| 736 | —CH₂—C(Cl)=CH₂ | 3 | 2-OCH₃ | H | O | CH | |
| 737 | —CH₂—CH=CH—CH₃ | 3 | 2-OCH₃ | H | O | CH | |
| 738 | —CH₂—CH=CH—CH₃ | 3 | 2-OCH₃ | H | O | N | |
| 739 | —CH₂—CH=CH₂ | 5 | 2-OCH₃ | H | O | N | |
| 740 | —CH₂—CH=CH₂ | 5 | 2-OCH₃ | H | O | CH | |
| 741 | —CH₂—C(CH₃)=CH₂ | 5 | 2-OCH₃ | H | O | CH | |
| 742 | —CH₂—C(CH₃)=CH₂ | 5 | 2-OCH₃ | H | O | N | |
| 743 | —CH₂—CH=CH—CH₃ | 5 | 2-OCH₃ | H | O | N | |
| 744 | —CH₂—CH=CH—CH₃ | 5 | 2-OCH₃ | H | O | CH | |
| 745 | —CH₂—C(Cl)=CH₂ | 5 | 2-OCH₃ | H | O | CH | |
| 746 | —CH₂—C(Cl)=CH₂ | 5 | 2-OCH₃ | H | O | N | |
| 747 | —CH₂—CH=CH₂ | 3 | 5-Br | 2-OCH₃ | O | N | m.p. 258–259° |
| 748 | —CH₂—CH=CH₂ | 3 | 5-Br | 2-OCH₃ | O | CH | m.p. 156–167° |
| 749 | —CH₂—C(CH₃)=CH₂ | 3 | 5-Br | 2-OCH₃ | O | CH | |
| 750 | —CH₂—C(CH₃)=CH₂ | 3 | 5-Br | 2-OCH₃ | O | N | |
| 751 | —CH₂—CH=CH₂ | 3 | 5-COOCH₃ | 2-OCH₃ | O | N | |
| 752 | —CH₂—CH=CH₂ | 3 | 5-COOCH₃ | 2-OCH₃ | O | CH | |
| 753 | —CH₂—C(CH₃)=CH₂ | 3 | 5-COOCH₃ | 2-OCH₃ | O | CH | |
| 754 | —CH₂—C(CH₃)=CH₂ | 3 | 5-COOCH₃ | 2-OCH₃ | O | N | |
| 755 | —CH₂—CH=CH—CH₃ | 3 | 5-COOCH₃ | 2-OCH₃ | O | N | |
| 756 | —CH₂—CH=CH—CH₃ | 3 | 5-COOCH₃ | 2-OCH₃ | O | CH | |
| 757 | —CH₂—CH=CH₂ | 2 | 5-NO₂ | 3-CF₃ | O | N | |
| 758 | —CH₂—CH=CH₂ | 2 | 5-NO₂ | 3-CF₃ | O | CH | |
| 759 | —CH₂—CH=CH₂ | 2 | 5-NO₂ | 3-Cl | O | CH | |
| 760 | —CH₂—CH=CH₂ | 2 | 5-NO₂ | 3-Cl | O | N | |
| 761 | —CH(CH₃)—C=CH₂ | 2 | 5-NO₂ | 3-Cl | O | N | |

TABLE 6-continued

Structure: R2, R1 substituted benzene with SO2-NH-C(=O)-NH-C(=N)(N=)-heterocycle containing CH3, E, OCH3; with X-A substituent.

| No. | A | Position of —X—A | R₁ | R₂ | X | E | Physical data (°C.) |
|---|---|---|---|---|---|---|---|
| 762 | —CH—C(CH₃)=CH₂ | 2 | 5-NO₂ | 3-Cl | O | CH | |
| 763 | —CH₂—CH=CH₂ | 2 | 5-CF₃ | 3-NO₂ | O | CH | |
| 764 | —CH₂—CH=CH₂ | 2 | 5-CF₃ | 3-NO₂ | O | N | |
| 765 | —CH₂—CH=CH₂ | 2 | 5-CH₃ | 3-CH₃ | O | N | |
| 766 | —CH₂—CH=CH₂ | 2 | 5-CH₃ | 3-CH₃ | O | CH | |
| 767 | —CH₂—CH=CH—CH₃ | 2 | 5-CH₃ | 3-CH₃ | O | CH | |
| 768 | —CH₂—CH=CH—CH₃ | 2 | 5-CH₃ | 3-CH₃ | O | N | |
| 769 | —CH₂—CH=CH—CH₃ | 2 | 5-Cl | 3-NO₂ | O | N | |
| 770 | —CH₂—CH=CH—CH₃ | 2 | 5-Cl | 3-NO₂ | O | CH | |
| 771 | —CH₂—CH=CH₂ | 2 | 5-Cl | 3-NO₂ | O | CH | |
| 772 | —CH₂—CH=CH₂ | 2 | 5-Cl | 3-NO₂ | O | N | |
| 773 | —CH₂—CH=CH₂ | 2 | 5-Cl | 3-Cl | O | N | |
| 774 | —CH₂—CH=CH₂ | 2 | 5-Cl | 3-Cl | O | CH | |
| 775 | —CH₂—CH₂—OCH₃ | 2 | 5-Cl | 3-Cl | O | CH | |
| 776 | —CH₂—CH₂—OCH₃ | 2 | 5-Cl | 3-Cl | O | N | |
| 777 | —CH₂—OCH₃ | 2 | 5-Cl | 3-Cl | O | N | |
| 778 | —CH₂—OCH₃ | 2 | 5-Cl | 3-Cl | O | CH | |
| 779 | —CH₂—C(CH₃)=CH₂ | 2 | 5-Cl | 3-Cl | O | CH | |
| 780 | —CH₂—C(CH₃)=CH₂ | 2 | 5-Cl | 3-Cl | O | N | |
| 781 | —CH₂—CH=CH₂ | 2 | 5-Br | 3-OCH₃ | O | N | |
| 782 | —CH₂—CH=CH₂ | 2 | 5-Br | 3-OCH₃ | O | CH | |
| 783 | —CH₂—CH=CH₂ | 3 | 5-Br | 2-OCH₃ | O | CH | |
| 784 | —CH₂—CH=CH₂ | 3 | 5-Br | 2-OCH₃ | O | N | |
| 785 | —CH₂—CH=CH₂ | 2 | 5-COOCH₃ | 3-OCH₃ | O | N | |
| 786 | —CH₂—CH=CH₂ | 2 | 5-COOCH₃ | 3-OCH₃ | O | CH | |
| 787 | —CH₂—CH=CH₂ | 3 | 5-COOCH₃ | 2-OCH₃ | O | CH | |
| 788 | —CH₂—CH=CH₂ | 3 | 5-COOCH₃ | 2-OCH₃ | O | N | |
| 789 | —CH₂—C(CH₃)=CH₂ | 3 | 5-COOCH₃ | 2-OCH₃ | O | N | |
| 790 | —CH₂—C(CH₃)=CH₂ | 3 | 5-COOCH₃ | 2-OCH₃ | O | CH | |
| 791 | —CH₂—CH=CH₂ | 2 | 5-CH₃ | 3-Br | O | CH | |
| 792 | —CH₂—CH=CH₂ | 2 | 5-CH₃ | 3-Br | O | N | |
| 793 | —CH₂—OCH₃ | 2 | 5-CH₃ | 3-Br | O | N | |
| 794 | —CH₂—OCH₃ | 2 | 5-CH₃ | 3-Br | O | CH | |
| 795 | —CH₂—CH=CH₂ | 2 | 5-Br | 3-NO₂ | O | N | |
| 796 | —CH₂—CH=CH₂ | 2 | 5-Br | 3-NO₂ | O | CH | |
| 797 | —CH₂—CH=CH₂ | 2 | 5-Cl | 3-Br | O | CH | |
| 798 | —CH₂—CH=CH₂ | 2 | 5-Cl | 3-Br | O | N | m.p. 175° |
| 799 | —CH₂—C(CH₃)=CH₂ | 2 | 5-Cl | 3-Br | O | N | |
| 800 | —CH₂—C(CH₃)=CH₂ | 2 | 5-Cl | 3-Br | O | CH | |
| 801 | —CH₂—CH₂—O—CH₃ | 2 | 5-Cl | 3-Br | O | CH | |
| 802 | —CH₂—CH₂—O—CH₃ | 2 | 5-Cl | 3-Br | O | N | |
| 803 | —CH₂—O—CH₃ | 5 | 2-NO₂ | H | O | CH | |
| 804 | —CH₂—O—CH₃ | 3 | H | H | S | CH | |
| 805 | —CH₂—CH₂—OCH₃ | 2 | 5-OC₂H₄—OCH₃ | H | O | N | |
| 806 | —CH₂—CH=CH₂ | 2 | 5-OCH₂—CH=CH₂ | H | O | N | |
| 807 | —CH₂—OCH₃ | 2 | 5-OCH₂—OCH₃ | H | O | N | |

TABLE 6-continued

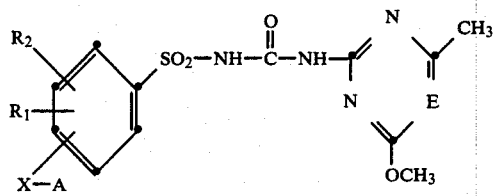

| No. | A | Position of —X—A | R₁ | R₂ | X | E | Physical data (°C.) |
|---|---|---|---|---|---|---|---|
| 808 | —CH₂—CH₂—OCH₃ | 2 | 5-S—C₂H₄—OCH₃ | H | S | N | |
| 809 | —CH₂—SCH₃ | 2 | 5-S—CH₂—SCH₃ | H | S | N | |
| 810 | —CH₂SO—CH₃ | 2 | 5-S—CH₂—SOCH₃ | H | S | N | |
| 811 | —CH₂—SO₂—CH₃ | 2 | 5-CH₂—SO₂—CH₃ | H | S | N | |

FORMULATION EXAMPLES

Example 4

Formulation Examples for liquid active ingredients of the formula I (throughout, percentages are by weight)

| (a) Emulsifiable concentrates | (a) | (b) | (c) |
|---|---|---|---|
| active ingredient | 20% | 10% | 1% |
| calcium dodecylbenzenesulfonate | 5% | 4% | 2% |
| castor oil polyethylene glycol ether (36 moles of ethylene oxide) | 5% | 4% | 4% |
| cyclohexanone | 30% | 20% | — |
| xylene mixture | 40% | 62% | 93% |

Emulsions of any required concentration can be produced from such concentrates by dilution with water.

| (b) Solutions | (a) | (b) | (c) | (d) |
|---|---|---|---|---|
| active ingredient | 20% | 10% | 5% | 1% |
| ethylene glycol monomethyl ether | 30% | — | 50% | 50% |
| polyethylene glycol 400 | — | 70% | — | 20% |
| N—methyl-2-pyrrolidone | 50% | 20% | 44% | 28% |
| epoxidised coconut oil | — | — | 1% | 1% |

These solutions are suitable for application in the form of microdrops.

| (c) Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (d) Dusts | (a) | (b) |
|---|---|---|
| active ingredient | 91.0% | 1% |
| highly dispersed silicic acid | 1% | 5% |
| talcum | 98.9% | — |
| kaolin | — | 94% |

Dusts which are ready for use are obtained by intimately mixing the carriers with the active ingredient.

Example 5

Formulation examples for solid active ingredients of the formula I (throughout, percentages are by weight)

| (a) Wettable powders | (a) | (b) | (c) |
|---|---|---|---|
| active ingredient | 20% | 60% | 0.5% |
| sodium lignosulfonate | 5% | 5% | 5% |
| sodium laurylsulfate | 3% | — | — |
| sodium diisobutylnaphthalene-sulfonate | — | 6% | 6% |
| octylphenol polyethylene glycol ether (7-8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground is a suitable mill, affording wettable powders which can be diluted with water to give suspensions of the desired concentration.

| (b) Emulsifiable concentrate | (a) | (b) |
|---|---|---|
| active ingredient | 10% | 1% |
| octylphenol polyethylene glycol ether (4-5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| active ingredient | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| active ingredient | 10% | 1% |
| sodium lignosulfonate | 2% | 2% |
| carboxymethylcellulose | 1% | 1% |

| (d) Extruder granulate | (a) | (b) |
|---|---|---|
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| active ingredient | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| active ingredient | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| active ingredient | 5% |
| isopropylamine | 1% |
| octylphenol polyethylene glycol ether (78 moles of ethylene oxide) | 3% |
| water | 91% |

BIOLOGICAL EXAMPLES

Example 6

Preemergence herbicidal action

In a greenhouse, plant seeds are sown in flower pots of 12–15 cm diameter. Immediately after sowing, the surface of the soil is treated with an aqueous dispersion or solution of the compounds to be tested. Concentrations of 4 kg a.i./ha are employed. The pots are then kept in the greenhouse at 22°–25° C. and 50–70% relative humidity. The test is evaluated 3 weeks later in accordance with the following rating:

1 = plants totally withered
2–3 = very pronounced action
4–6 = medium action
7–8 = insignificant action
9 = no action (as untreated controls)

| Test Results (preemergence): | | | | |
|---|---|---|---|---|
| Action rate of application kg a.i./ha | Compound 601 | | | |
| Test plant | 0.25 | 0.12 | 0.06 | 0.03 |
| Wheat | 4 | 7 | 9 | 9 |
| Avena fatua | 2 | 2 | 3 | 4 |
| Alopecurus myos. | 2 | 2 | 2 | 2 |
| Echinochloa c.g. | 2 | 2 | 2 | 2 |
| Rottboellia ex. | 2 | 3 | 3 | 3 |
| Cyperus escul. | 3 | 3 | 3 | 3 |
| Cotton | 2 | 2 | 2 | 3 |
| Abutilon | 1 | 1 | 2 | 2 |
| Xanthium Sp. | 2 | 3 | 3 | 3 |
| Chenopodium Sp. | 1 | 1 | 2 | 2 |
| Ipomoea | 2 | 2 | 2 | 2 |
| Sinapis | 2 | 2 | 2 | 2 |
| Galium aparine | 2 | 2 | 2 | 3 |
| Viola tricolor | 2 | 2 | 2 | 2 |

Example 7

Postemergence herbicidal action (contact action)

A number of weeds and cultivated plants in pots, both monocots and dicots, are sprayed postemergence, in the 4- to 6-leaf stage, with an aqueous active ingredient dispersion at a rate of application of 4 kg a.i./ha, and then kept at 24°–26° C. and 45–60% relative humidity. The test is evaluated 15 days after treatment and the action is assessed in accordance with the same rating as in Example 6.

| Test Results (postemergence): | | | | |
|---|---|---|---|---|
| Action rate of application kg a.i./ha | Compound 601 | | | |
| Test plant | 0.25 | 0.12 | 0.06 | 0.03 |
| Wheat | 7 | 9 | 9 | 9 |
| Maize | 3 | 4 | 7 | 9 |
| Dry rice | 4 | 5 | 8 | 9 |
| Avena fatua | 4 | 5 | 8 | 9 |
| Alopecurus myos. | 1 | 2 | 2 | 2 |
| Echinochloa c.g. | 2 | 2 | 6 | 6 |
| Cyperus escul. | 4 | 5 | 9 | 9 |
| Cotton | 4 | 6 | 7 | 9 |
| Abutilon | 2 | 2 | 2 | 2 |
| Xanthium Sp. | 1 | 1 | 1 | 1 |
| Chenopodium Sp. | 1 | 2 | 2 | 2 |
| Ipomoea | 2 | 3 | 3 | 4 |
| Sinapis | 1 | 1 | 1 | 1 |
| Galium aparine | 1 | 2 | 2 | 2 |
| Viola tricolor | 2 | 2 | 2 | 2 |

Example 8

Inhibition of sprouting in stored potatoes

A number of commercially available potatoes of the "Urgenta" variety, without sprouts, are washed and dried. The potatoes are then immersed in emulsions of the compounds to be tested in different concentrations, placed on filter paper in plastic dishes, and kept in the dark at 14°–21° C. and 50% relative humidity. Evaluation is made 34 days after application.

The percentage weight loss of the tubers and the weight of the sprouts compared with untreated controls are simultaneously determined. A number of the compounds of formula I inhibited sprouting completely in this test. At the same time, the weight loss of the potatoes was less than 10% of the weight loss of the control potatoes.

Example 9

Growth inhibition of tropical cover crops

The test plants (*centrosema plumieri* and *centrosema pubescens*) are reared until fully grown and then cut back to a height of 60 cm. The plants are sprayed 7 days later with an aqueous emulsion of the compound to be tested. The test plants are kept at 705 relative humidity and 6000 lux artificial light for 14 hours per day, at day temperatures of 27° C. and night temperatures of 21° C. The test is evaluated 4 weeks after application.

The new growth in comparison with the control is assessed and the phytotoxicity is determined. In this test, new growth of plants treated with a number of compounds of the formula I is markedly reduced (less than 20%), without damage being caused to the test plants.

What is claimed is:

1. A compound of the formula

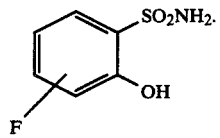

2. The compound according to claim 1 which is 5-fluoro-2-hydroxybenzosulfonamide.